(12) United States Patent
Hatano et al.

(10) Patent No.: US 10,123,714 B2
(45) Date of Patent: Nov. 13, 2018

(54) MAGNETIC MEASUREMENT APPARATUS

(71) Applicant: Renesas Electronics Corporation, Kawasaki-shi, Kanagawa (JP)

(72) Inventors: Yuji Hatano, Kanagawa (JP); Koji Yamada, Kanagawa (JP); Takashi Yoshino, Kanagawa (JP)

(73) Assignee: Renesas Electronics Corporation, Koutou-ku, Tokyo (JP)

( * ) Notice: Subject to any disclaimer, the term of this patent is extended or adjusted under 35 U.S.C. 154(b) by 571 days.

(21) Appl. No.: 14/748,563

(22) Filed: Jun. 24, 2015

(65) Prior Publication Data

US 2015/0374250 A1 Dec. 31, 2015

(30) Foreign Application Priority Data

Jun. 26, 2014 (JP) .................................. 2014-131944

(51) Int. Cl.

| | |
|---|---|
| *A61B 5/04* | (2006.01) |
| *A61B 5/00* | (2006.01) |
| *C30B 29/04* | (2006.01) |
| *G01R 33/00* | (2006.01) |
| *G01R 33/032* | (2006.01) |
| *G01R 33/12* | (2006.01) |

(52) U.S. Cl.
CPC ........ *A61B 5/04008* (2013.01); *A61B 5/0071* (2013.01); *C30B 29/04* (2013.01); *G01R 33/0094* (2013.01); *G01R 33/032* (2013.01); *G01R 33/1284* (2013.01)

(58) Field of Classification Search
CPC ................................................. A61B 5/04008
See application file for complete search history.

(56) References Cited

U.S. PATENT DOCUMENTS

| | | | |
|---|---|---|---|
| 2010/0308813 A1 | 12/2010 | Lukin et al. | |
| 2014/0191139 A1* | 7/2014 | Englund | .......... G01N 33/48728 250/459.1 |
| 2015/0276754 A1 | 10/2015 | Shirakawa et al. | |

FOREIGN PATENT DOCUMENTS

| | | |
|---|---|---|
| JP | 2011-180570 A | 9/2011 |
| WO | 2014/058012 A1 | 9/2016 |

OTHER PUBLICATIONS

S. Steinert et al., "High sensitivity magnetic imaging using an array of spins in diamond," Review of Scientific Instruments, 2010, pp. 043705-1-043705-5, vol. 81.
Ryuji Igarashi et al., "Real-Time Background-Free Selective Imaging of Fluorescent Nanodiamonds in Vivo," Nano Letters, Oct. 2012, pp. 5726-5732, vol. 12.
Notification of Reasons for Refusal dated Aug. 1, 2017 issued by the Japanese Patent Office in counterpart in counterpart application No. 2014-131944.

\* cited by examiner

*Primary Examiner* — Rochelle Turchen
(74) *Attorney, Agent, or Firm* — Sughrue Mion, PLLC

(57) ABSTRACT

High-accuracy magnetic measurement is performed by efficiently using nitrogen-vacancy pairs in all orientations. A magnetic measurement apparatus includes a diamond crystal and an image sensor. The diamond crystal has nitrogen-vacancy pairs. The image sensor detects the intensities of fluorescence generated by an exciting light applied to the diamond crystal by using a plurality of pixels. The nitrogen-vacancy pairs of the diamond crystal are made to one-to-one correspond to the pixels. The fluorescence generated by one nitrogen-vacancy pair is received by one pixel made to correspond to the nitrogen-vacancy pair.

7 Claims, 16 Drawing Sheets

MAGNETIC MEASUREMENT APPARATUS

CROSS-REFERENCE TO RELATED APPLICATION

The present application claims priority from Japanese Patent Application No. 2014-131944 filed on Jun. 26, 2014, the content of which is hereby incorporated by reference into this application.

TECHNICAL FIELD OF THE INVENTION

The present invention relates to a magnetic measurement apparatus and, more particularly, to a technique effective in detecting a magnetic field in a room temperature atmosphere by using nitrogen-vacancy pairs of a diamond crystal.

BACKGROUND OF THE INVENTION

As a biomagnetic measurement system as medical equipment, for example, a magnetoencephalography system is known. The magnetoencephalography system is a system which accurately examines an active region and the degree of activity in the brain by externally measuring a weak magnetic field generated by neurons.

A biomagnetic measurement system of this type includes a high-sensitivity magnetic measurement apparatus. As this high-sensitivity magnetic measurement apparatus, a SQUID (Superconducting Quantum Interference Device) is used, which can detect a weak biological vector magnetic field such as brain magnetism. However, a cryogenic environment is required for the operation of this device.

On the other hand, as a high-sensitivity magnetic field measurement apparatus which can operate in a room temperature atmosphere, a diamond crystal containing nitrogen-vacancy pairs has been proposed (see, for example, non-patent document 1).

Non-patent document 1 (S. Steinert, F. Dolde, P. Neumann, A. Aird, B. Naydenov, G. Balasubramanian, F. Jelezko, and J. Wrachtrup; "High sensitivity magnetic imaging using an array of spins in diamond", Review of Scientific Instrument 81, 043705-1 to 5 (2010)) discloses the following contents. Green laser light is used as a blue-green light source which applies exciting light to a diamond crystal as a sensor for measuring a magnetic field, and a CCD array is used to detect a red fluorescence output from the diamond crystal. A magnetic field is measured from the minimum fluorescence intensity value of the microwave frequency dependence of the red fluorescence intensity obtained by sweeping the frequency of microwaves applied to the diamond crystal.

In addition, for example, non-patent document 2 (R. Igarashi, Y. Yoshinari, H. Yokota, T. Sugi, F. Sugihara, K. Ikeda, H. Sumiya, S. Tsuji, I. Mori, H. Tochio, Y. Harada, M. Shirakawa; "Real-time background-free selective imaging of fluorescent nanodiamonds in vivo", Nano Letters nl302979, October 2012, pp 5726-5732.) discloses a technique of observing a fluorescence output from a single nitrogen-vacancy pair using an SIP (Selective Imaging Protocol) technique. The SIP technique is a technique of removing background noise containing fluorescence other than fluorescence from nitrogen-vacancy pairs by selectively measuring only red fluorescence from nitrogen-vacancy pairs.

SUMMARY OF THE INVENTION

Non-patent document 1 discloses the microwave frequency dependence of the red fluorescence intensity acquired by sweeping the frequency of the microwaves applied to a diamond crystal (FIG. 2A). This waveform is measured as the superimposition of four types of waveforms. The document describes that the four types originate from the fact that the vacancy of each nitrogen-vacancy pair can have four types of orientations with respect to the diamond crystal orientation when viewed from the nitrogen.

In this case, a magnetic field is measured as the positional change of a "valley" corresponding to a minimum fluorescence intensity value of this waveform. Therefore, the narrower and deeper the "valley" becomes, the higher the measurement accuracy becomes. However, a waveform originating from each nitrogen-vacancy pair has "valleys" at different positions with respect to the four types of orientations of the vacancy when viewed from the nitrogen.

For this reason, in general, a measured waveform is the superimposition of the "valleys" at these four different types of positions. Thus, the number of nitrogen-vacancy pairs contributing to the depth of a "valley" is larger than that with one type but is smaller than the total number of nitrogen-vacancy pairs with respect to the four types. That is, not all the nitrogen-vacancy pairs can be used for measurement. This may make it impossible to perform high-accuracy magnetic measurement.

Non-patent document 1 describes that magnetic sensitivity is proportional to $\sqrt{N}$, where N is the number of effective nitrogen-vacancy pairs. For this reason, it is preferable to use all the nitrogen-vacancy pairs instead of only the largest number of nitrogen-vacancy pairs among those corresponding to the four types.

The above and other objects and novel characteristics of the present invention will be apparent from the description of the present specification and the accompanying drawings.

A magnetic measurement apparatus according to an embodiment includes a diamond crystal having a plurality of nitrogen-vacancy pairs, and an image sensor configured to detect a fluorescence intensity generated by an exciting light applied to the diamond crystal by using a plurality of pixels. The nitrogen-vacancy pairs of the diamond crystal are made to one-to-one correspond to the pixels, and fluorescence generated by one of the nitrogen-vacancy pairs is received by one of the pixels made to correspond to the nitrogen-vacancy pair.

(1) It is possible to improve the detection accuracy of a magnetic field.

(2) It is possible to improve the efficiency of magnetic field measurement.

BRIEF DESCRIPTIONS OF THE DRAWINGS

DESCRIPTIONS OF THE PREFERRED EMBODIMENTS

Figure 1:
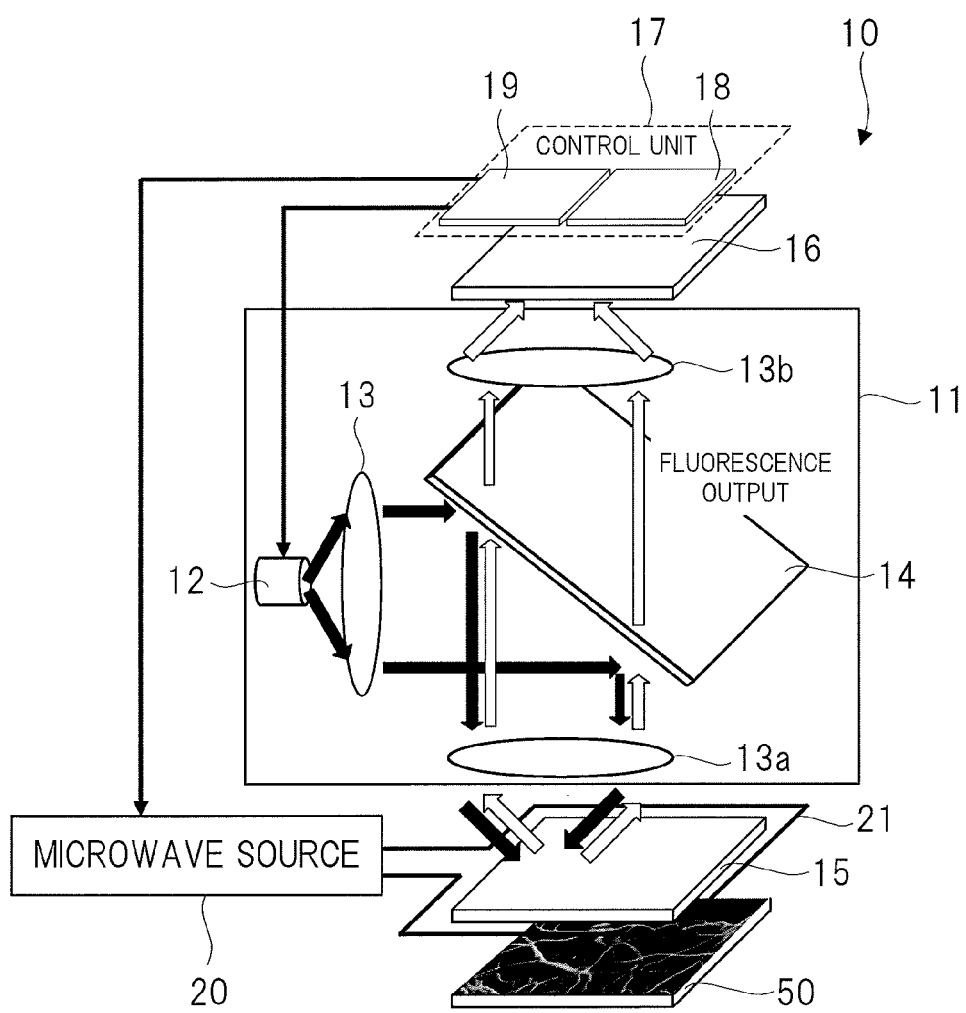
FIG. 1 is an explanatory view showing an example of the configuration of a magnetic measurement apparatus according to a first embodiment.

The following embodiment will be described being divided into a plurality of embodiments or sections for convenience sake if necessary, but unless expressly stated otherwise, these embodiments or sections are not independent from one another, where one thereof is in a relationship with a modification example, details, a supplementary explanation, or the like of a portion or entirety of the other.

Also, in the embodiments described below, when referring to the number of elements (including number of pieces, values, amount, range, etc.), the number of the elements is not limited to a specific number unless otherwise stated or except the case where the number is apparently limited to a specific number in principle. The number larger or smaller than the specified number is also applicable.

Further, in the embodiments described below, it goes without saying that the components (including element steps) are not always indispensable unless otherwise stated or except the case where the components are apparently indispensable in principle.

Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Note that components having the same function are denoted by the same reference symbols throughout the drawings for describing the embodiments, and the repetitive description thereof will be omitted. Further, hatching is used in some cases even in a plan view so as to make the drawings easy to see.

Hereinafter, the embodiments will be described in detail.

(First Embodiment)

<Brief Description>

According to a brief description of this embodiment, in a magnetic measurement apparatus 10, the positions of nitrogen-vacancy pairs 25 in a diamond crystal 15 one-to-one correspond to the positions of pixels 26 of an image sensor 16 which measures fluorescence outputs from the nitrogen-vacancy pairs 25. In other words, the image sensor 16 is provided such that fluorescence generated by a given one of the nitrogen-vacancy pairs 25 is received by one pixel 26 made to correspond to the nitrogen-vacancy pair 25.

In addition, the magnetic measurement apparatus 10 is calibrated in advance for each nitrogen-vacancy pair so as to specify what type of orientation the vacancy of each nitrogen-vacancy pair 25 has when viewed from the nitrogen with respect to the diamond crystal orientation. The magnetic measurement apparatus 10 is configured to measure a magnetic field so as to improve the measurement accuracy by efficiently using all the nitrogen-vacancy pairs having four types of orientations.

Furthermore, it is possible to extract fluorescence outputs from nitrogen-vacancy pairs having the same orientation by making the positions of the nitrogen-vacancy pairs one-to-one correspond to the pixel positions on the image sensor 16 which measures fluorescence outputs from the nitrogen-vacancy pairs 25. By using this, a feedback operation is performed by integrating the differences between pixel outputs from the image sensor 16, which measures outputs from a given group of nitrogen-vacancy pairs, when microwaves are applied and when no microwaves are applied, and inputting the integrated value to the microwave source so as to keep the integrated value constant. This can make the entire measurement time effectively contribute to magnetic field measurement, thereby improving the measurement accuracy.

<Example of Configuration of Magnetic Measurement Apparatus>

FIG. 1 is an explanatory view showing an example of the configuration of the magnetic measurement apparatus 10 according to a first embodiment.

The magnetic measurement apparatus 10 is a biomagnetic detector used in medical equipment such as a magnetoencephalograph, magnetocardiograph, or magneto-myograph, which is a biomagnetic measurement apparatus. For example, a magnetoencephalograph noninvasively measures and analyzes, from the scalp, a weak magnetic field generated accompanying a cerebral nerve activity.

As shown in FIG. 1, the magnetic measurement apparatus 10 includes a light source unit 11, the diamond crystal 15, the image sensor 16, a control unit 17, a microwave source 20, and a coil 21.

The light source unit 11 is constituted by a blue-green light source 12, lenses 13, 13a, and 13b, and a dichroic mirror 14. The blue-green light source 12 outputs exciting light having a wavelength shorter than, for example, 530 nm.

The lens 13 condenses exciting light output from the blue-green light source 12. The dichroic mirror 14 is an optical element which reflects only light having a specific wavelength and transmits light having other wavelengths, thereby separating exciting light from fluorescence.

The dichroic mirror 14 is arranged at an angle of, for example, about 45° with respect to incident light. This causes exciting light entering from the lens 13 to be reflected by the dichroic mirror 14. That is, the exciting light is bent at 90° and guided downward.

The lens 13a is provided below the dichroic mirror 14. The diamond crystal 15 and a specimen 50 as a measurement target are arranged below the lens 13a. The lens 13a condenses the exciting light reflected by the dichroic mirror 14 and irradiates the diamond crystal 15 with the light. The fluorescence generated from the diamond crystal 15 is transmitted through the dichroic mirror 14.

The lens 13b is provided above the dichroic mirror 14. The image sensor 16 is provided above the lens 13b. The lens 13b condenses the fluorescence generated from the diamond crystal 15 and irradiates the image sensor 16 with the light. The image sensor 16 is, for example, a semiconductor sensor such as a CCD (Charge Coupled Device), and captures a fluorescence image generated from the diamond crystal 15.

The fluorescence image captured by the image sensor 16 is output to the control unit 17 serving as a signal processing unit. The control unit 17 includes a signal processing circuit 18 and a control circuit 19. The signal processing circuit 18 and the control circuit 19 are formed on, for example, a semiconductor chip.

The signal processing circuit 18 processes the input fluorescence image. The control circuit 19 is connected to the image sensor 16, the blue-green light source 12, and the microwave source 20, and supplies timing signals to the image sensor 16, the blue-green light source 12, and the microwave source 20. In addition, the control circuit 19 performs control to set a microwave frequency in the microwave source 20.

The coil 21 is connected to the microwave source 20. The microwave source 20 and the coil 21 will be referred to as microwave units. The coil 21 is configured to surround a peripheral portion of the diamond crystal 15 in the form of a loop. The microwave source 20 energizes the coil 21 with a microwave current. This generates a microwave magnetic field around the diamond crystal 15. Note that the frequency of microwaves output from the microwave source 20 is set by the control circuit 19, as described above.

<Examples of Configurations of Diamond Crystal and Image Sensor>

Figure 2:
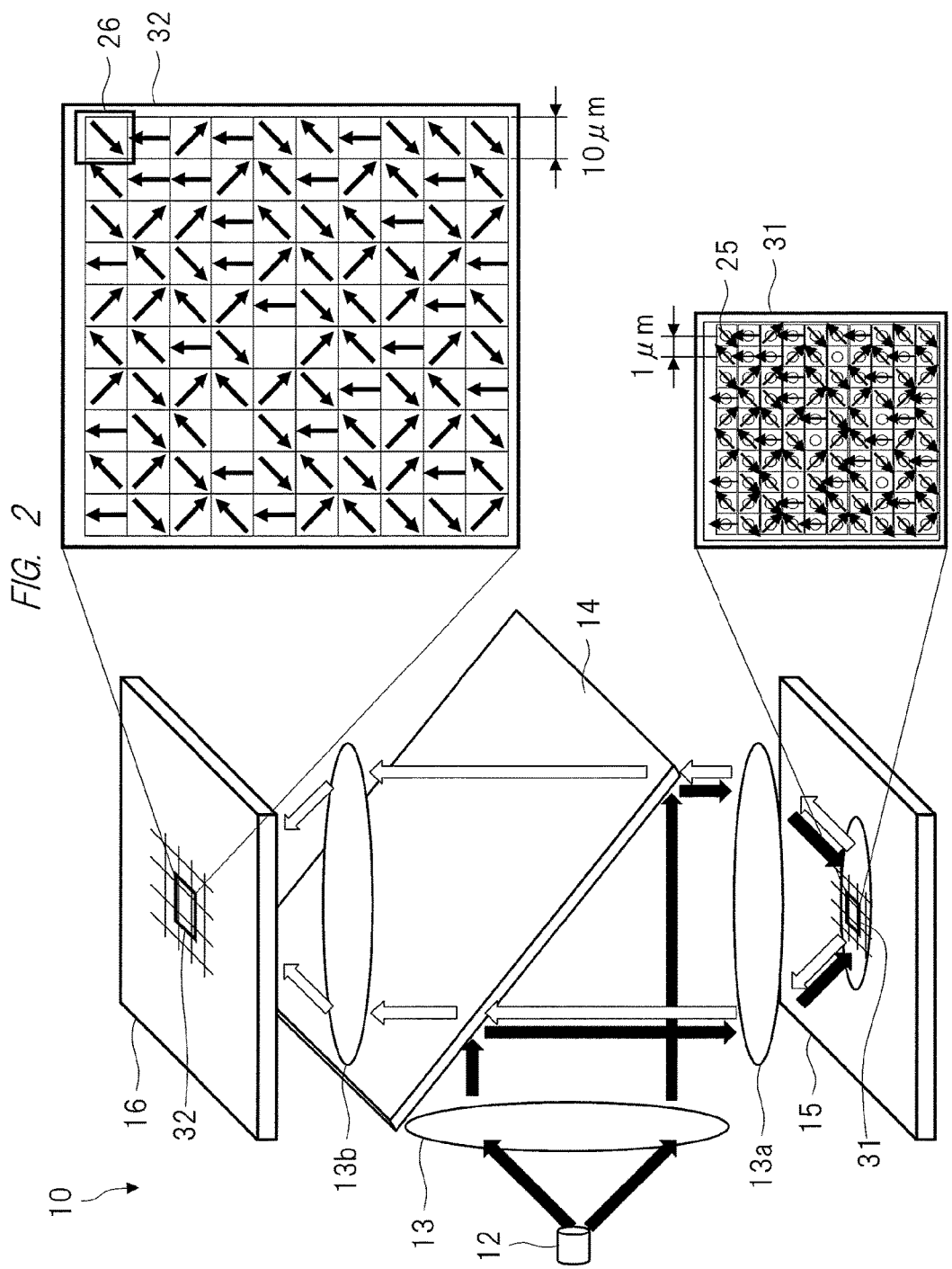
FIG. 2 is an explanatory view showing examples of the configurations of a diamond crystal and image sensor provided in the magnetic measurement apparatus in FIG. 1.

FIG. 2 is an explanatory view showing examples of the configurations of the diamond crystal 15 and image sensor 16 provided in the magnetic measurement apparatus 10 in FIG. 1.

Note that FIG. 2 shows an example of an enlarged view of a portion of the surface of the diamond crystal 15 at a lower right position, and shows an example of an enlarged view of a portion of the surface of the image sensor 16 at an upper right position.

The diamond crystal 15 is a single crystal. As shown at the lower right in FIG. 2, the nitrogen-vacancy pairs 25 are regularly arranged in a lattice pattern by microfabricating the surface. The intervals between the nitrogen-vacancy pairs 25 are, for example, about 1 µm.

The image sensor 16 has the pixels 26 as light-receiving elements regularly arranged in a lattice pattern. The intervals between the pixels 26 are, for example, about 10 µm.

The nitrogen-vacancy pairs 25 in the diamond crystal 15 are regularly arranged in a square lattice pattern, and so are the pixels 26 of the image sensor 16 which measures fluorescence outputs from the nitrogen-vacancy pairs 25. For this reason, properly designing the optical system extending from the surface of the diamond crystal 15 to the image sensor 16 can make fluorescence outputs generated by the respective nitrogen-vacancy pairs 25 one-to-one correspond to the respective pixels 26 of the image sensor 16.

The one-to-one correspondence indicates that the uniformity of the aspect ratio of the diamond crystal 15 and coordinates of the nitrogen-vacancy pairs 25, i.e., the configuration of the equal intervals between the nitrogen-vacancy pairs 25 which match the configuration intervals of the pixels 26 of the image sensor 16, is implemented so as to respectively project fluorescence points generated from, for example, the N×N nitrogen-vacancy pairs 25 onto the pixels 26 of the N×N image sensor 16. The aspect ratio of the diamond crystal 15 is typically one to one. This one-to-one correspondence will be described later.

As described in the summary of the invention, the vacancy of each nitrogen-vacancy pair 25 has four types of orientations when viewed from the nitrogen with respect to the orientation of the diamond crystal 15. The processing measuring the orientations in advance will be referred to as pre-calibration processing hereinafter. Note that each of the four types of arrows written in each pixel 26 of the image sensor 16 shown at the upper right in FIG. 2 indicates which one of the four types of orientations the vacancy of the corresponding nitrogen-vacancy pair 25 has when viewed from the nitrogen.

In the pre-calibration processing of measuring the orientation of the vacancy of each nitrogen-vacancy pair 25 when viewed from the nitrogen so as to indicate which one of the four types of orientations the vacancy has with respect to the diamond crystal orientation, the microwave frequency dependence of the intensity of the red fluorescence generated by the nitrogen-vacancy pair 25 is measured by sweeping the frequency of microwaves applied to the diamond crystal 15 while the external magnetic field from the microwave source 20 in FIG. 1 is applied.

Collation with a simulation value will reveal an orientation. This simulation value can be obtained by the technique disclosed in, for example, Figure S2 in non-patent document 2.

In this case, an external magnetic field is applied to the diamond crystal 15 first in one direction in a uniform size with respect to the overall crystal. The external magnetic field is generated by, for example, supplying a DC current to a coil arranged near/around the diamond crystal 15 or arranging a permanent magnet near it.

It is possible to simulate the position of a "valley" of microwave frequency dependence of red fluorescence intensity with respect to each of the four types of orientation of the nitrogen-vacancy pairs 25 from the relative relationship between the orientation of the diamond crystal itself and the applied direction of a magnetic field.

Comparing with a measured value can confirm which one of the four types of orientations each nitrogen-vacancy pair 25 has. Note that since the orientation of each nitrogen-vacancy pair 25 does not change at room temperature, the above pre-calibration processing is only required to be performed once before the assembly of the magnetic measurement apparatus 10 shown in FIG. 1.

As described above, the diamond crystal 15 is a single crystal. When the diamond crystal 15 is a single crystal, there can be no orientation other than the four types of orientations shown in FIG. 5 described later. In addition, the relative relationship between the four types of orientations is fixed as a direction in which each vertex is viewed from the center of a regular tetrahedron. For this reason, when actually determining the orientation of each lattice point, it is only required to measure to which one of the four orientations the orientation of the lattice point is the nearest, but it is not required to accurately measure an angle. This can facilitate pre-calibration processing.

In contrast to this, when the diamond crystal is not a single crystal but is a polycrystal constituted by a plurality of crystal regions, although the four types of orientations in the respective crystal regions are fixed, the respective orientations among the different crystal regions have an arbitrary relationship. This complicates pre-calibration processing.

FIG. 2 shows, at the upper right, that the four types of orientations of the nitrogen-vacancy pairs 25 in a region 31 as part of the surface of the diamond crystal 15 are respectively imaged on the pixels 26 in a region 32 as part of the image sensor 16.

Note that in the case shown in FIG. 2, for example, the nitrogen-vacancy pairs 25 are formed at 10 (vertical)×10 (horizontal) lattice positions in the region 31 of the diamond crystal 15, and 10 (vertical)×10 (horizontal) pixels 26 exist in the region 32 of the image sensor 16 accordingly. Note that lattice elements in which no nitrogen-vacancy pairs are formed are allowed to exit in the region 31.

The orientation of each nitrogen-vacancy pair 25 is specified by performing the above pre-calibration processing in advance before the measurement of a magnetic field in the specimen 50 in FIG. 1. Thereafter, when measuring a magnetic field in the specimen 50, it is possible to correct the differences among the four types of orientations of the nitrogen-vacancy pairs 25.

This makes it possible to use all the four types of orientations of the respective nitrogen-vacancy pairs 25 for the measurement of a magnetic field, and hence to improve the measurement accuracy.

In this case, the microwave frequency dependence of the intensity of the red fluorescence generated by each nitrogen-vacancy pair 25 changes in accordance with a scalar magnetic field in the orientation of the vacancy when viewed from the nitrogen. That is, on a waveform with the abscissa representing the microwave frequency, and the ordinate representing the red fluorescence intensity, the frequency difference between the two "valleys" appearing at symmetrical positions with respect to a frequency of 2.87 GHz is proportional to the scalar magnetic field.

Since it is possible to measure scalar magnetic fields in four directions by using the nitrogen-vacancy pairs 25 in the four types of orientations, it is possible to measure vector magnetic fields on the diamond crystal surface.

<Example of Correspondence between Pixels and Nitrogen-Vacancy Pairs>

Figure 3:
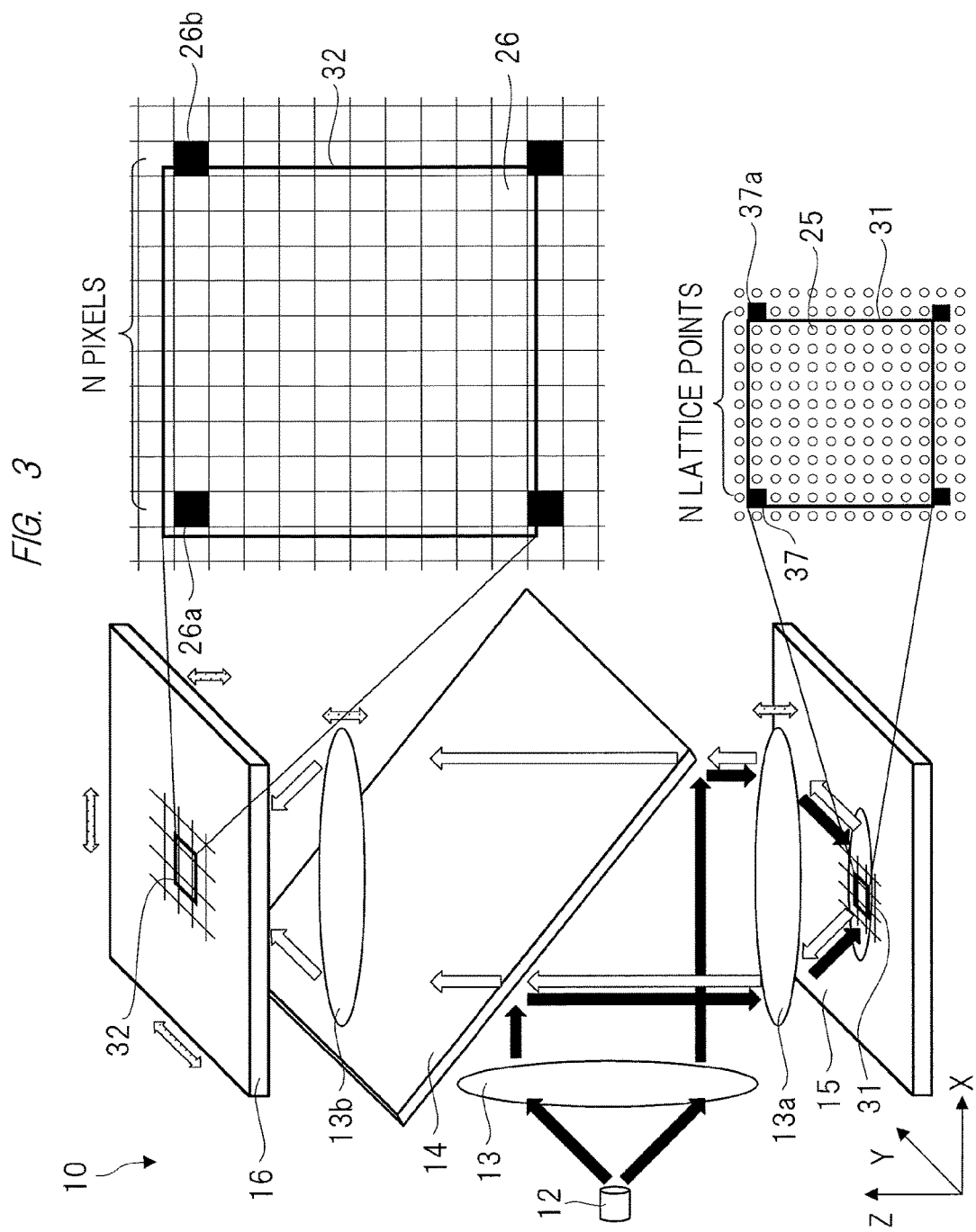
FIG. 3 is an explanatory view showing an example of the one-to-one correspondence between the pixels of the image sensor and the nitrogen-vacancy pairs of the diamond crystal in the magnetic measurement apparatus in FIG. 1.

FIG. 3 is an explanatory view showing an example of the one-to-one correspondence between the pixels 26 of the image sensor 16 and the nitrogen-vacancy pairs 25 of the diamond crystal 15 in the magnetic measurement apparatus 10 in FIG. 1.

FIG. 3 shows, on the lower right, the region 31 which is an enlarged view of a given portion of the surface of the diamond crystal 15, and shows, on the upper right, the region 32 which is an enlarged view of a portion of the surface of the image sensor 16 which corresponds to the region 31.

A marker 37 is arranged in the region 31 of the diamond crystal 15 in advance. The marker 37 is formed on the surface of the diamond crystal 15 by, for example, a microfabrication technique so as to be optically identifiable.

For descriptive convenience, assume that the lattice obtained by microfabricating the surface of the diamond crystal 15 to arrange the nitrogen-vacancy pairs 25 thereon is arranged along the X- and Y-axes, and a direction perpendicular to the surface is defined as the Z-axis.

This configuration makes it possible to finely adjust the lenses 13a and 13b in the Z-axis direction and the image sensor 16 in three axis directions, namely, the X-, Y-, and Z-axis directions in the optical system extending from the surface of the diamond crystal 15 to the image sensor 16 through the lens 13a, the dichroic mirror 14 and the lens 13b.

First of all, fine adjustment is made to form an image of the marker 37 on one pixel 26a of the image sensor 16. Subsequently, fine adjustment is performed again to form an image of a marker 37a separated from the marker 37 by N lattice points on a pixel 26b separated from the pixel 26a by N pixels.

Repeating this operation can make the respective nitrogen-vacancy pairs 25 provided in a lattice pattern to one-to-one correspond to the respective pixels 26 of the image sensor 16. With this configuration, the fluorescence generated by an arbitrary nitrogen-vacancy pair 25 is received by one pixel 26 made to correspond to the nitrogen-vacancy pair 25.

<Example of Block-by-Block Correspondence>

Figure 4:
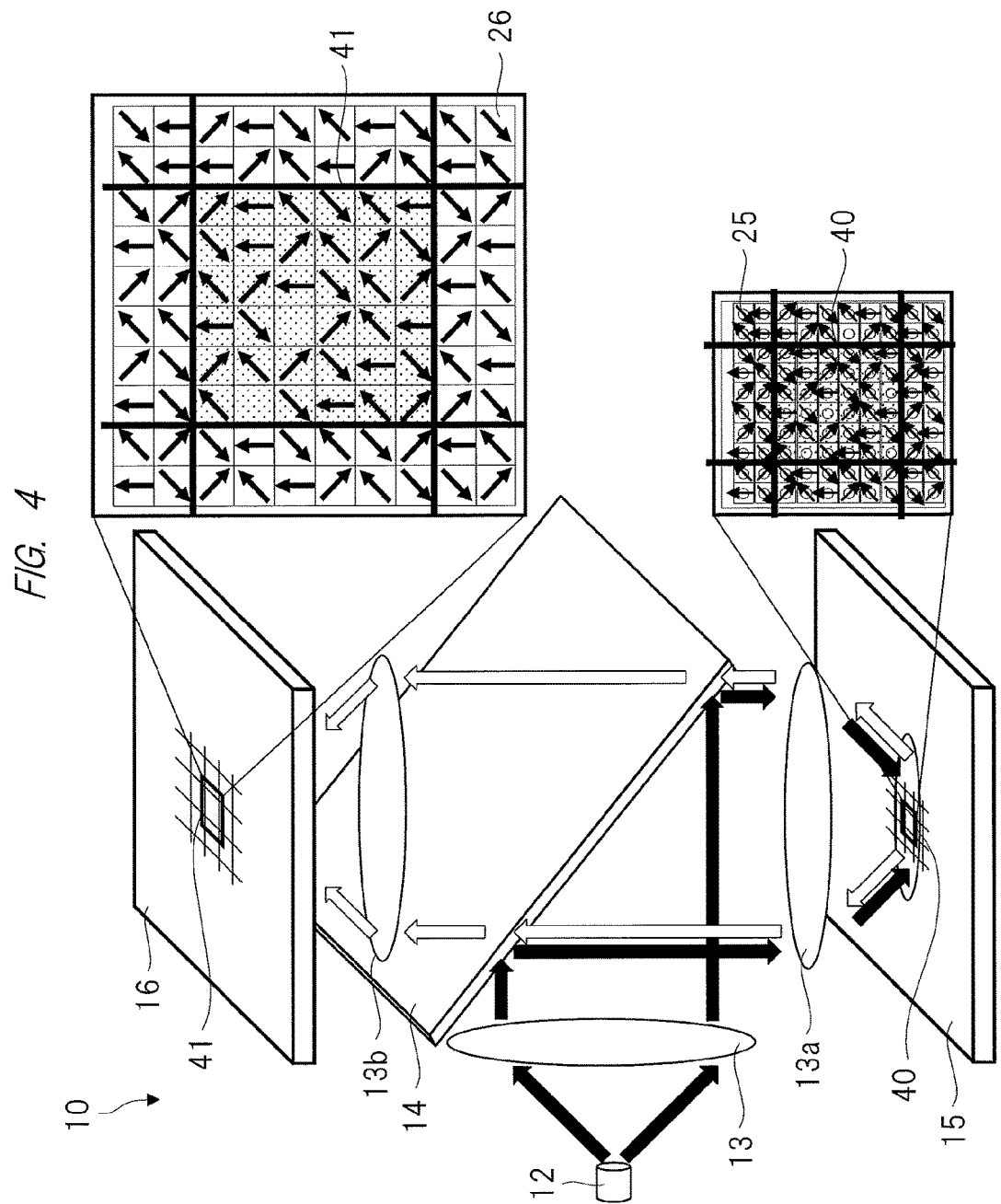
FIG. 4 is an explanatory view showing an example of the block-to-block correspondence between the diamond crystal and the image sensor in the magnetic measurement apparatus in FIG. 1.

FIG. 4 is an explanatory view showing an example of block-by-block correspondence between the diamond crystal 15 and the image sensor 16 in the magnetic measurement apparatus 10 in FIG. 1.

In general, in image processing in an image sensor, it is possible to reduce noise in tradeoff with a spatial resolution by averaging output signals from the image sensor on a block basis over a plurality of pixels. The above block-based averaging is also effective for the magnetic measurement apparatus 10 in FIG. 1.

In this case, a block 40 shown on the lower right in FIG. 4 is a block having a plurality of nitrogen-vacancy pairs 25 (in the case in FIG. 4, 6×6 nitrogen-vacancy pairs 25) on the diamond crystal 15 shown on the lower left in FIG. 4. A block 41 shown on the upper right in FIG. 4 is a block on the image sensor 16 shown on the upper left in FIG. 4. Note that the block 40 is a block on the diamond crystal 15, and the block 41 is a block on the image sensor 16.

The block 41 on the image sensor 16 corresponds to the block 40 on the diamond crystal 15. The respective nitrogen-vacancy pairs 25 in the block 40 on the diamond crystal 15 respectively correspond to the pixels 26 in the block 41 on the image sensor 16.

Note however that since the nitrogen-vacancy pairs 25 corresponding to the respective pixels 26 have the four types of orientations (to be indicated by the arrows in FIG. 4 hereinafter), a beneficial effect can be obtained by averaging for noise reduction for each of the four types of orientations.

<Orientations of Nitrogen-Vacancy Pairs>

Figure 5:
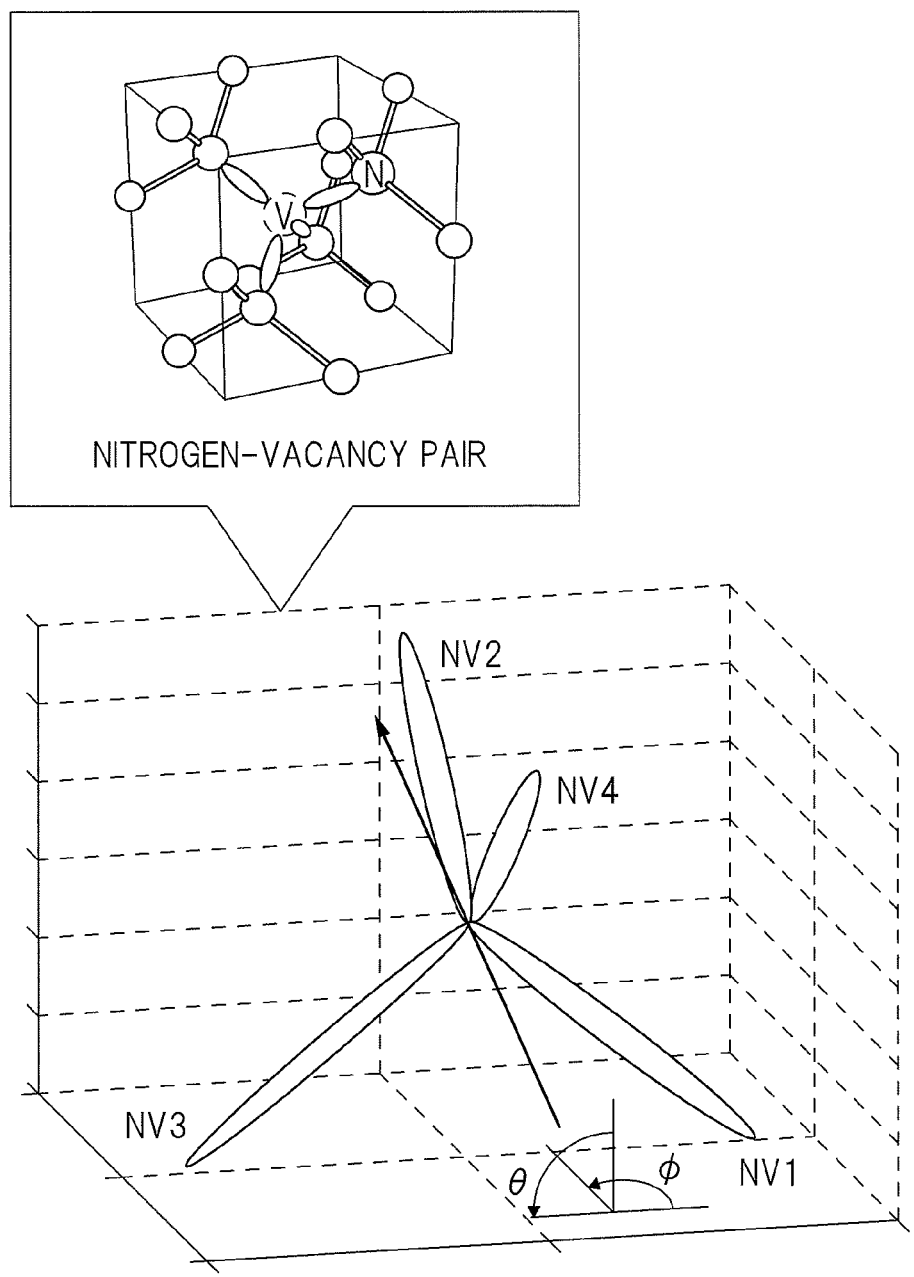
FIG. 5 is an explanatory view schematically showing the four types of orientations of a nitrogen-vacancy pair described in non-patent document 1.

FIG. 5 is an explanatory view schematically showing the four types of orientations of the nitrogen-vacancy pairs 25 described in non-patent document 1.

For descriptive convenience, the four types of orientations of the nitrogen-vacancy pairs 25 are respectively referred to as orientations NV1, NV2, NV3, and NV4, as shown in FIG. 5. The diamond crystal 15 is a cubic system, and hence the four types of orientations NV1 to NV4 respectively extend from the barycenter of the regular tetrahedron toward the four vertices. Referring to FIG. 5, these four orientations will be respectively referred to as the orientations NV1 to NV4. In addition, the four orientations can be arbitrarily named.

Referring to FIG. 5, the nitrogen-vacancy pair 25 directed in the orientation NV1 detects a scalar magnetic field in the orientation NV1. For this reason, the scalar magnetic field in the orientation NV1 is measured from the microwave frequency dependence of the red fluorescence intensity detected in the pixel 26 corresponding to the nitrogen-vacancy pair 25 directed in the orientation NV1.

With regard to the pixel 26 corresponding to the nitrogen-vacancy pair 25 directed in the orientation NV1, the scalar magnetic field in the orientation NV1 is measured as a numerical value with noise reduced by averaging in the block 41 from the waveform obtained by averaging the microwave frequency dependence of the red fluorescence intensity in the block 41.

Likewise, with regard to the pixel 26 corresponding to the nitrogen-vacancy pair 25 directed in the orientation NV2, the scalar magnetic field in the orientation NV2 is measured as a numerical value with noise reduced by averaging in the block 41 from the waveform obtained by averaging the microwave frequency dependence of the red fluorescence intensity in the block 41.

In addition, with regard to the pixel 26 corresponding to the nitrogen-vacancy pair 25 directed in the orientation NV3, the scalar magnetic field in the orientation NV3 is measured as a numerical value with noise reduced by averaging in the block 41 from the waveform obtained by averaging the microwave frequency dependence of the red fluorescence intensity in the block 41.

Furthermore, with regard to the pixel 26 corresponding to the nitrogen-vacancy pair 25 directed in the orientation NV4, the scalar magnetic field in the orientation NV4 is measured as a numerical value with noise reduced by averaging in the block 41 from the waveform obtained by averaging the microwave frequency dependence of the red fluorescence intensity in the block 41.

<Example of Noise Reduction>

A noise reduction technique using the magnetic measurement apparatus 10 will be described next with reference to FIGS. 6 and 7.

Figure 6:
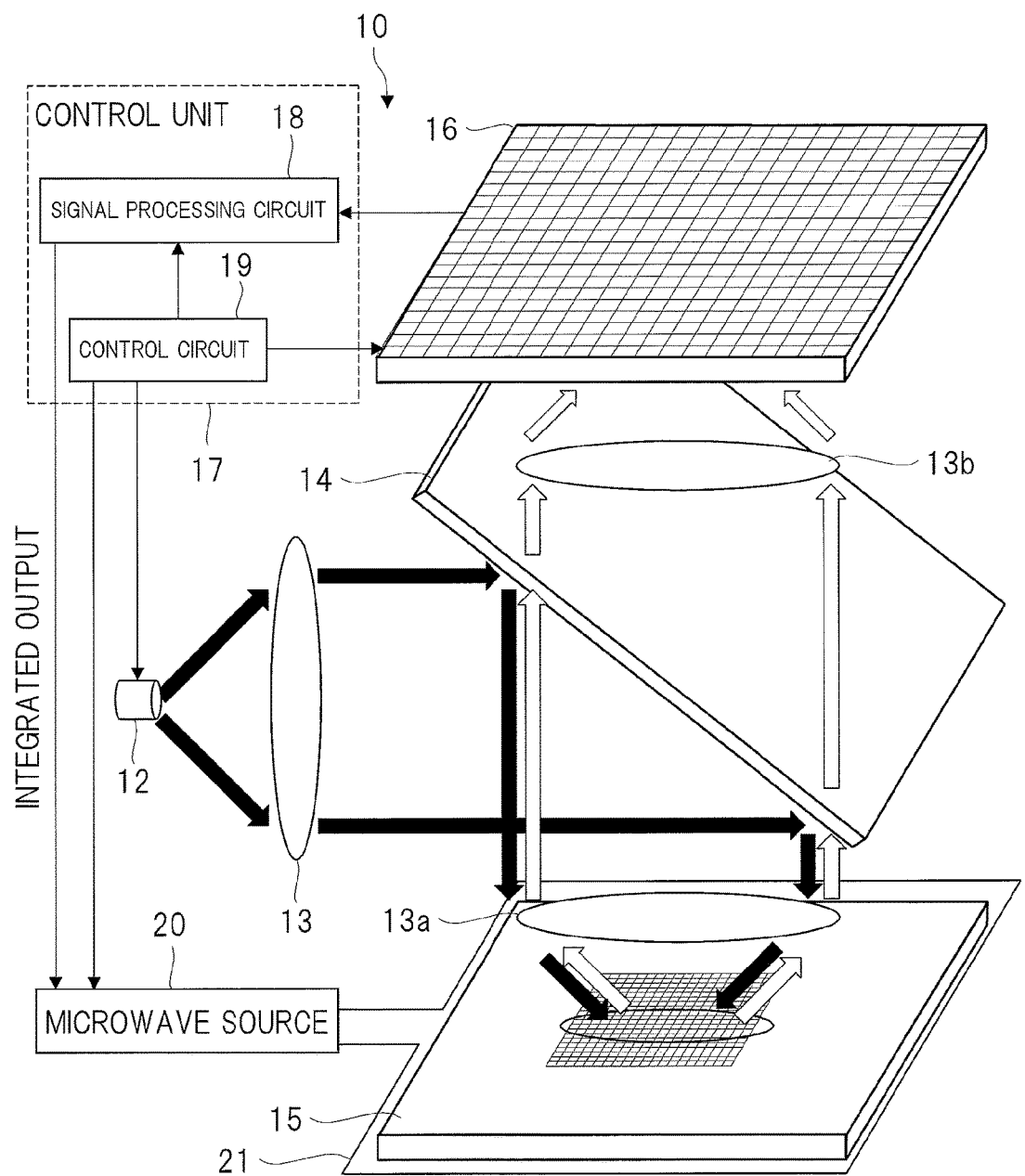
FIG. 6 is an explanatory view showing an example of a concrete configuration for the implementation of a spatial resolution on a pixel basis by the magnetic measurement apparatus in FIG. 1.

FIG. 6 is an explanatory view showing an example of a concrete configuration for the implementation of a spatial resolution on a pixel basis by the magnetic measurement apparatus 10 in FIG. 1. FIG. 7 is a graph showing an example of a waveform near lower fluorescence intensity points of the microwave frequency spectrum of the fluorescence intensity from the nitrogen-vacancy pair 25. Referring to FIG. 7, the abscissa represents the frequency of microwaves output from the microwave source 20, and the ordinate represents the fluorescence intensity. In addition, referring to FIG. 7, the steepest slope of a waveform near a lower fluorescence intensity point will be referred to as a slope 53. The slope 53 shifts laterally in the frequency axis direction depending on the value of a magnetic field.

Figure 7:
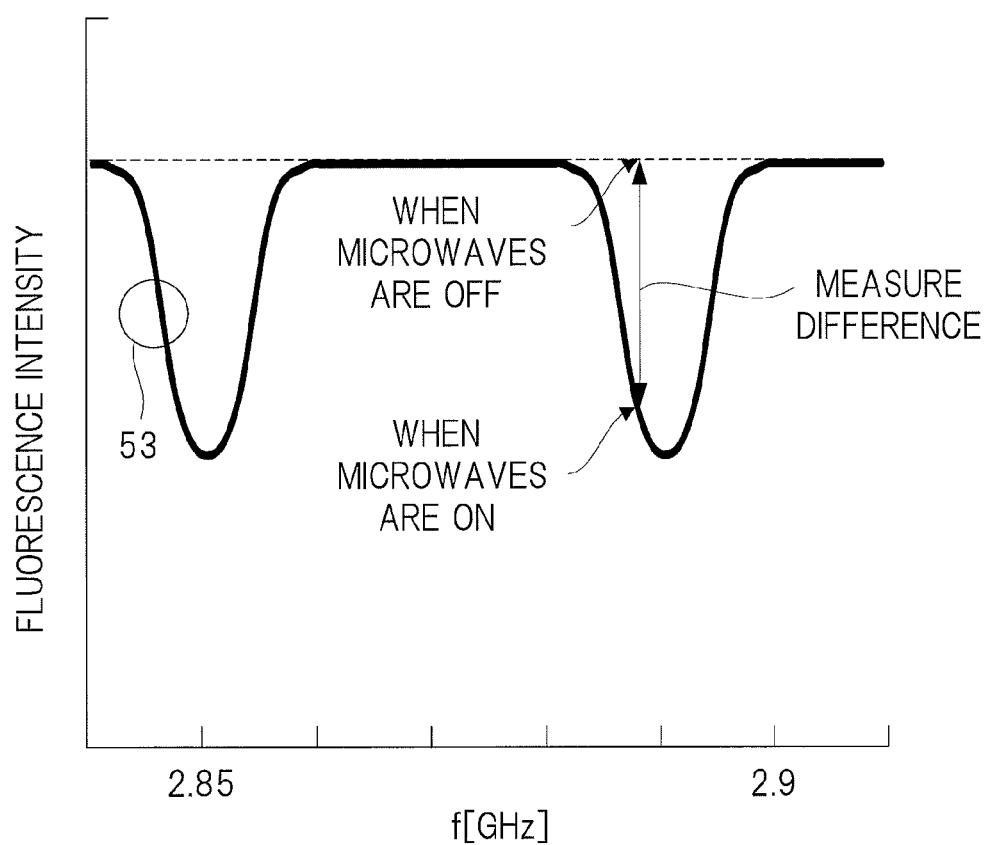
FIG. 7 is a graph showing an example of a waveform near lower fluorescence intensity points of the microwave frequency spectrum of the fluorescence intensity from a nitrogen-vacancy pair.

The waveform shown in FIG. 7 shows two "valleys". If, however, there is no magnetic field, the two "valleys" overlap into one centered on about 2.87 GHz. It is known that, although two "valleys" are separated from each other in the presence of a magnetic field, the relationship between the shift of a "valley" on the frequency axis and the magnetic field intensity in the orientation of a nitrogen-vacancy pair is defined by 28.07 GHz/T (Tesla) (see, for example, non-patent document: Y. Yoshinari et al., "Observing the rotational diffusion of nanodiamonds with arbitrary nitrogen vacancy center configurations", PHYSICAL REVIEW B 88, 235206 (2013)).

An arbitrary one pixel of the image sensor 16 will be described below with reference to FIG. 6.

Referring to FIG. 6, the signal processing circuit 18 feeds back the integrated output of the differences between the intensities of fluorescence from nitrogen-vacancy pairs measured by the pixels of the image sensor 16 with irradiation with microwaves and those without irradiation with microwaves as a frequency correction value for the microwaves generated by the microwave source 20 so as to make the differences constant.

For calibration, the frequency position of the slope 53 shown in FIG. 7 without the application of a magnetic field is recorded as an initial value, and a frequency correction value after the application of a magnetic field is measured. This makes it possible to read the value of the magnetic field detected by each pixel of the image sensor 16 as the difference between the corrected frequency and the initial value.

While the above feedback function is operating, a change in magnetic field intensity can be detected as a change in microwave frequency.

An operation of this feedback function will be described below with reference to FIGS. 8 to 10.

<Examples of Configurations of Control Unit and Microwave Source>

Figure 8:
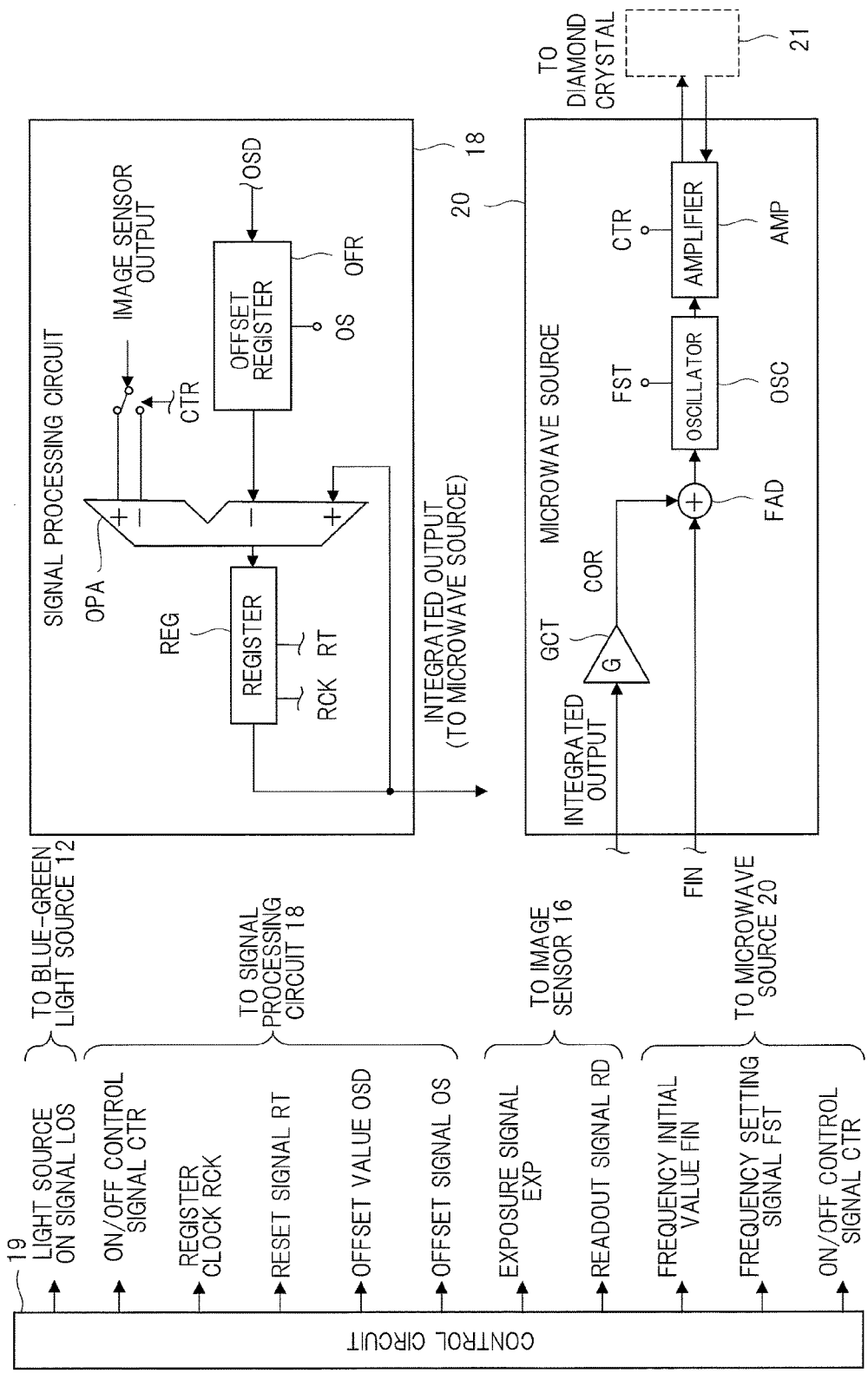
FIG. 8 is an explanatory view showing an example of the connection configuration of a signal processing circuit, a control circuit, and a microwave source provided in the magnetic measurement apparatus in FIG. 1.

FIG. 8 is an explanatory view showing an example of the connection configuration of the signal processing circuit 18, the control circuit 19, and the microwave source 20 provided in the magnetic measurement apparatus 10 in FIG. 1.

The signal processing circuit 18 includes an offset register OFR, an operation unit OPA, and a register REG. The operation unit OPA has the first to fourth operation input terminals. The first and fourth operation input terminals differ in polarity from the second and third operation input terminals. In this case, the first and fourth operation input terminals are positive (+) input terminals, and the second and third operation input terminals are negative (−) input terminals.

An output signal from a pixel of the image sensor 16 is input to the first and second operation input terminals. An output signal from the offset register OFR is input to the third operation input terminal. An output signal from the register REG is input to the fourth operation input terminal.

The operation unit OPA adds an output signal from a pixel of the image sensor 16 and an output signal from the register REG, and subtracts an ON/OFF control signal CTR output from the control circuit 19 and an output signal from the offset register OFR. The operation unit OPA then outputs the resultant signal to the register REG.

The offset register OFR captures an offset value OSD output from the control circuit 19 at the timing of an offset signal OS output from the control circuit 19, and outputs the offset value to the third operation input terminal of the operation unit OPA.

The output destination of the signal output from a pixel of the image sensor 16 is controlled based on the ON/OFF control signal CTR output from the control circuit 19. As a result, as described above, the signal is output to either the first operation input terminal or the second operation input terminal of the operation unit OPA.

The register REG captures signals output from the operation unit OPA to obtain an integrated output based on a register clock RCK output from the control circuit 19, and outputs the integrated output to the fourth operation input terminal of the operation unit OPA. In addition, the register REG is reset by a reset signal RT output from the control circuit 19.

The microwave source 20 includes a gain adjuster GCT, a frequency adder FAD, an oscillator OSC, and an amplifier AMP. The gain adjuster GCT multiplies an integrated output from the signal processing circuit 18 by, for example, a gain G and outputs the resultant value as a frequency correction value COR.

The frequency adder FAD adds a frequency initial value FIN output from the control circuit 19 and the frequency correction value COR output from the gain adjuster GCT, and outputs the addition value to the oscillator OSC.

Based on a frequency setting signal FST output from the control circuit 19, the oscillator OSC outputs microwaves with the frequency value designated by the addition value from the frequency adder FAD to the amplifier AMP. The amplifier AMP amplifies the microwaves output from the oscillator OSC and irradiates the diamond crystal 15 with the microwaves. The microwave irradiation is ON/OFF-controlled by the ON/OFF control signal CTR output from the control circuit 19.

The control circuit 19 supplies a light source ON signal LOS to the blue-green light source 12, and supplies an exposure signal EXP and a readout signal RD to the image sensor 16. In addition, as described above, the control circuit 19 outputs the ON/OFF control signal CTR, the register clock RCK, the reset signal RT, the offset value OSD, the offset signal OS, the frequency initial value FIN, and the frequency setting signal FST.

Figure 9:
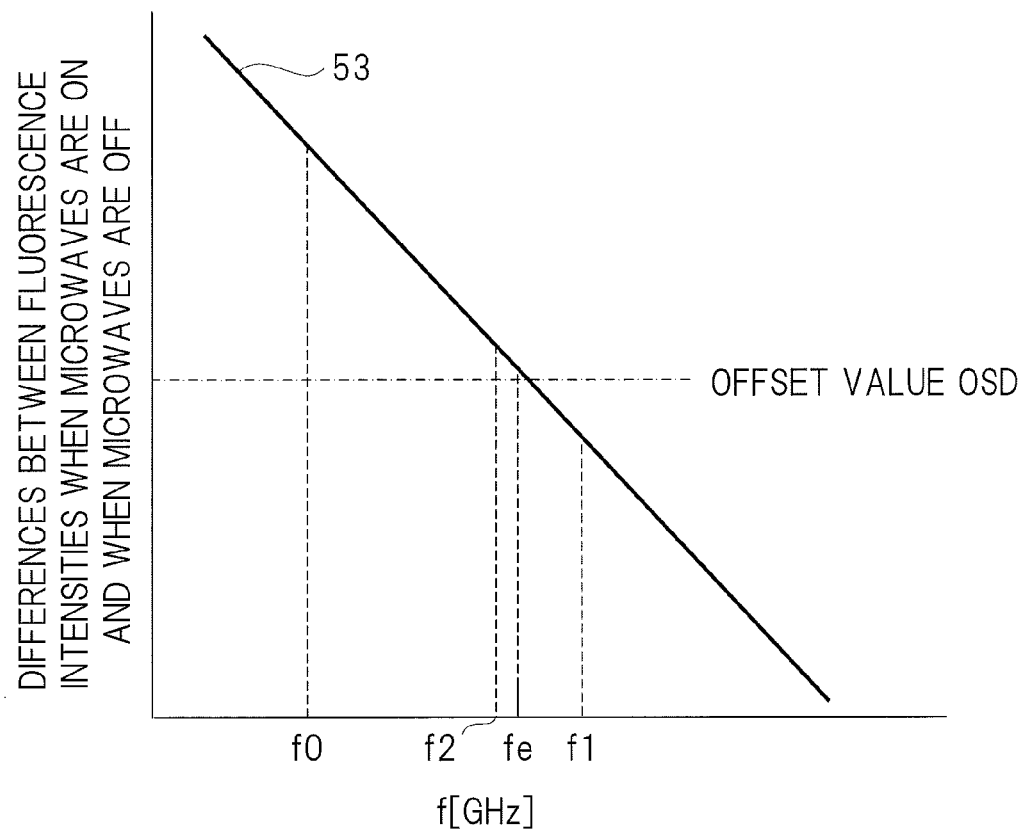
FIG. 9 is a graph showing an example of a waveform around the steepest slope adjacent to a lower fluorescence intensity point among the waveforms near the lower fluorescence intensity points of the microwave frequency spectrum of the fluorescence intensity from the nitrogen-vacancy pair shown in FIG. 7.

FIG. 9 is a graph showing an example of a waveform around the steepest slope adjacent to a lower fluorescence intensity point among the waveforms near the lower fluorescence intensity points of the microwave frequency spectrum of the fluorescence intensity from the nitrogen-vacancy pair shown in FIG. 7.

Referring to FIG. 9, the abscissa represents the output frequency of the oscillator OSC, and the ordinate represents the difference between fluorescence intensities when microwaves are on and when microwaves are off.

The slope 53 shown in FIG. 9 is the steepest slope of the microwave frequency spectrum of the fluorescence intensity from the nitrogen-vacancy pair. Referring to FIG. 9, when a frequency value corresponding to the offset value OSD output from the control circuit 19 is expressed as a frequency fe and the initial value of the output frequency of the oscillator OSC is expressed as a frequency f0, the initial value of the output frequency changes to a frequency f1 and a frequency f2, at every timing of the frequency setting signal FST output from the control circuit 19, and then converges to the frequency fe.

<Operations of Control Circuit and Microwave Source>

Figure 10:
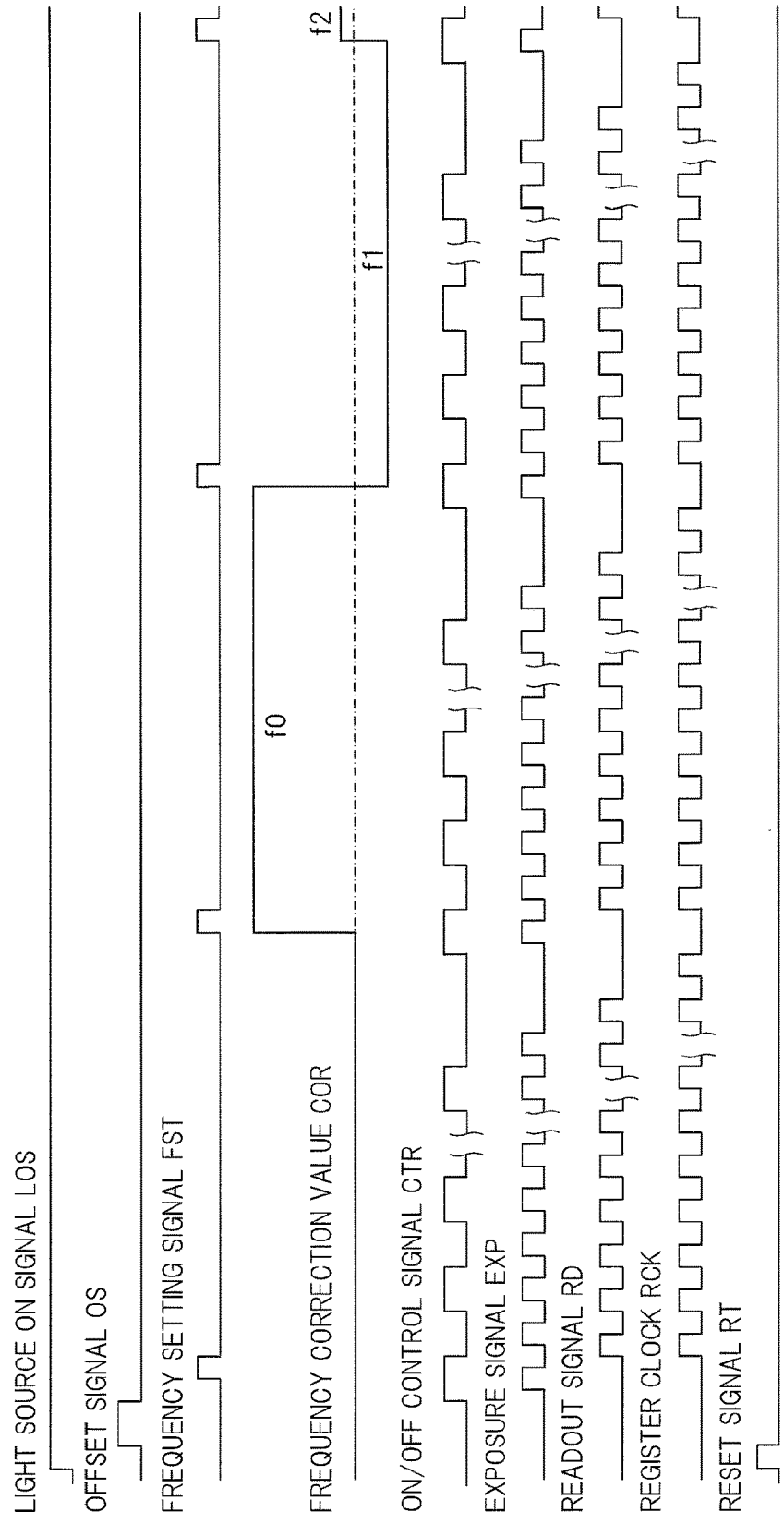
FIG. 10 is a timing chart showing an example of the timing of each signal in the control circuit and microwave source shown in FIG. 8.

FIG. 10 is a timing chart showing an example of the timing of each signal in the control circuit 19 and the microwave source 20 shown in FIG. 8.

FIG. 10 shows, from above to below, the output timing of each of the following signals: the light source ON signal LOS, the offset signal OS, the frequency setting signal FST, the frequency correction value COR, the ON/OFF control signal CTR, the exposure signal EXP, the readout signal RD, the register clock RCK, and the reset signal RT. Note that, as described above, the frequency correction value COR is output from the gain adjuster GCT, and the remaining signals are output from the control circuit 19.

FIG. 10 shows a process in which after the register REG is initialized by applying the light source ON signal LOS, the initial value of the output frequency of the oscillator OSC converges to the frequency fe as an equilibrium value, as shown in FIG. 9.

After the application of the light source ON signal LOS, the register REG is reset by the reset signal RT, and the integrated output from the signal processing circuit 18 and the frequency correction value COR output from the gain adjuster GCT each become a zero value.

Subsequently, the offset register OFR reads the offset value OSD based on the offset signal OS output from the control circuit 19. The frequency of the oscillator OSC is then set by the frequency setting signal FST output from the control circuit 19. At this time point, however, the frequency initial value FIN supplied by the control circuit 19 is set as it is. The ON/OFF control signal CTR from the control circuit 19 is input to the amplifier AMP to ON/OFF-control microwave irradiation.

The exposure signal EXP from the control circuit 19 is applied while the ON/OFF control signal CTR stably has a constant value. The readout signal RD from the control circuit 19 is applied at the timing when the ON/OFF control signal CTR changes. At this timing, the operation unit OPA reads a pixel signal output from the image sensor 16.

In this case, pixel signal output from the image sensor 16 are respectively read into the operation input terminals of different polarities, i.e., the first operation input terminal and the second operation input terminal, when microwaves are on and when microwaves are off, respectively.

For this reason, after one cycle of the ON/OFF control signal CTR, the difference between pixel signal outputs from the image sensor 16 when microwaves are on and when microwaves are off is input to the register REG.

An output from the register REG is fed back to the fourth operation input terminal of the operation unit OPA. Therefore, after N cycles of the ON/OFF control signal CTR, the value obtained by N-cycle integration is output as an integrated output to the microwave source 20. Upon reflection of this output, when the next frequency setting signal FST is applied, the frequency correction value COR output from the gain adjuster GCT becomes the frequency f0.

Subsequently, as similar processing is repeated, the frequency correction value COR output from the gain adjuster GCT changes to the frequency f1 and the frequency f2, and converges to the frequency fe.

Note that when there is no need to implement a spatial resolution, i.e., when it is required to measure only a magnetic field at the position of a specific pixel, or when it is required to measure only an average magnetic field at a position corresponding to one group of pixels, the image sensor 16 can use the entire measurement time for integration. That is, the noise reduction efficiency is high.

When performing magnetic field measurement with respect to all the pixels of the image sensor 16 on a pixel basis, it is necessary to measure magnetic fields with respect to the pixels 26 one by one serially. Assume that the number of pixels of the image sensor is, for example, N×N, and the time required for the convergence of the integration of one pixel is represented by T, the time required to perform magnetic field measurement with respect to all the pixels is given by N×N×T.

In this case, the signal processing circuit 18 integrates differences when microwaves are applied and when no microwaves are applied instead of integrating image sensor pixel outputs themselves in order to remove background noise including fluorescence other than that from nitrogen-vacancy pairs (see, for example, the SIP (Selective Imaging Protocol) technique disclosed in non-patent document 2).

As described above, performing pre-calibration processing by performing one-to-one correspondence between the nitrogen-vacancy pairs 25 of the diamond crystal 15 and the pixels 26 of the image sensor 16 makes it possible to use all the four types of orientations of the nitrogen-vacancy pairs 25. It is therefore possible to improve the accuracy of magnetic measurement.

In addition, since the signal processing circuit 18 can implement a spatial resolution on a pixel basis, it is possible to improve the efficiency of magnetic measurement.

(Second Embodiment)

<Brief Description>

The magnetic measurement apparatus 10 in FIG. 6 according to the above first embodiment is configured to implement a spatial resolution on a pixel basis in the image sensor 16. In contrast to this, a second embodiment will exemplify a case in which a spatial resolution is implemented on a block basis in an image sensor 16.

<Example of Configuration of Magnetic Measurement Apparatus>

Figure 11:
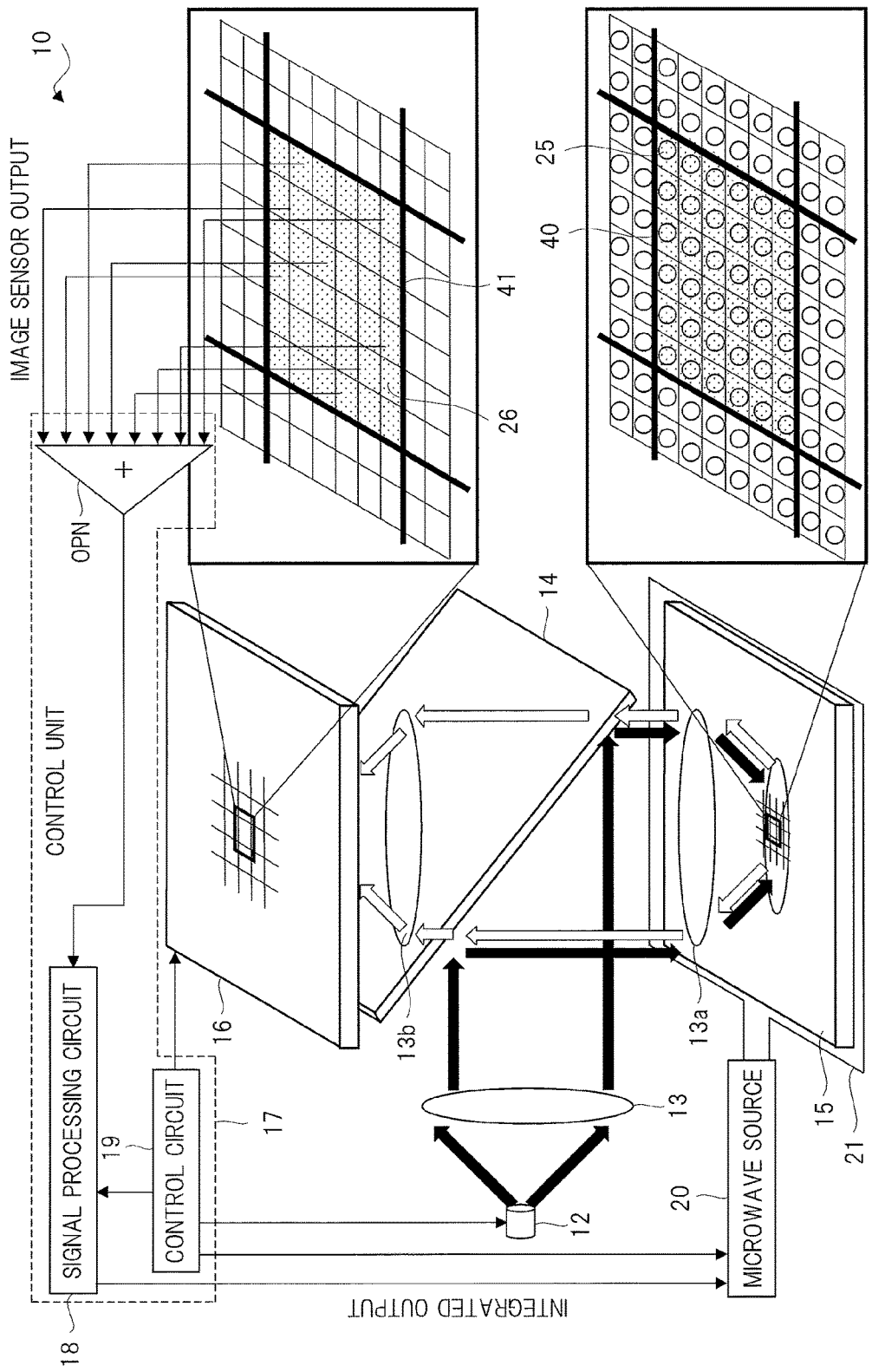
FIG. 11 is an explanatory view showing an example of the configuration of a magnetic measurement apparatus according to a second embodiment.

FIG. 11 is an explanatory view showing an example of the configuration of a magnetic measurement apparatus 10 according to the second embodiment.

The magnetic measurement apparatus 10 in FIG. 11 implements a spatial resolution on a block basis in the image sensor 16 by performing negative feedback control with respect to a pixel output from the image sensor 16 as a frequency modulation input to a microwave source 20.

The magnetic measurement apparatus 10 in FIG. 11, as in FIG. 6, includes a blue-green light source 12, a lens 13, a dichroic mirror 14, a diamond crystal 15, the image sensor 16, a control unit 17, a microwave source 20, and a coil 21.

In addition, the control unit 17 is newly provided with an operation unit OPN in addition to the configuration constituted by a signal processing circuit 18 and a control circuit 19 in FIG. 6. The operation unit OPN is provided between the signal processing circuit 18 and the image sensor 16.

Referring to FIG. 11, the operation unit OPN symbolically represents the processing of adding pixel outputs from the image sensor 16 corresponding to nitrogen-vacancy pairs 25 having the same orientation. In actual processing, the operation unit OPN adds outputs which are read out from a portion corresponding to nitrogen-vacancy pairs 25 having the same orientation among the outputs serially read out from the respective pixels of the image sensor 16.

In each each block 41 of the image sensor 16, the orientations of the respective nitrogen-vacancy pairs 25 of the diamond crystal 15 are known by the pre-calibration processing described in the first embodiment. Therefore, the control circuit 19 can specify pixels 26 corresponding to nitrogen-vacancy pairs 25 having the same orientation, and hence outputs control signals to the operation unit OPN so as to select only signals from the pixels 26 specified for each block 41.

The signals output from the operation unit OPN are input to an operation unit OPA of the signal processing circuit 18. In this manner, the signal processing circuit 18 has received a group of pixel outputs from the image sensor 16 which correspond to nitrogen-vacancy pairs 25 having the same orientation in the block 41, and feeds back frequency modulation inputs to the microwave source 20 so as to keep constant the integrated value of differences when microwaves are applied and when no microwaves are applied. Note that the circuit configuration of the signal processing circuit 18 is the same as that shown in FIG. 8, and hence the description will be omitted.

Assume that the number of pixels of the image sensor 16 is, for example, N×N, the size of the block 41 of the image sensor 16 is, for example, n×n, and the time required for the convergence of the integration of one pixel 26 is represented by T. In this case, the time required for magnetic field measurement with respect to all the pixels is given by N/n×N/n×T×4. In this case, "×4" is required to independently perform measurement with respect to the four orientations of nitrogen-vacancy pairs 25 in the block 41.

<Example of Configuration of Block Size>

Figure 12:
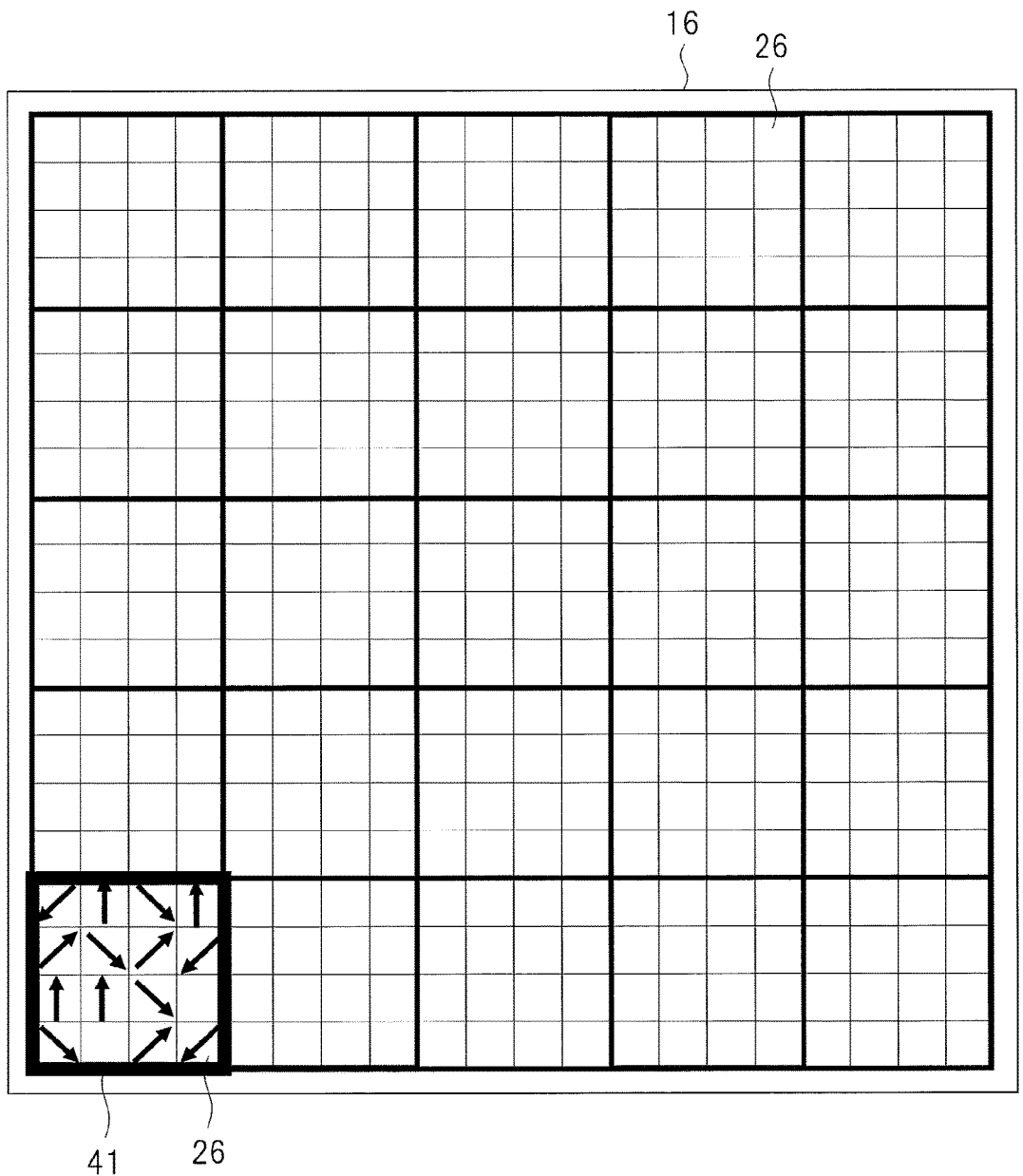
FIG. 12 is an explanatory view showing an example of the configuration of the number of pixels and block size of an image sensor used in the magnetic measurement apparatus in FIG. 11.

FIG. 12 is an explanatory view showing an example of the configuration of the number of pixels and block size of the image sensor 16 used in the magnetic measurement apparatus 10 in FIG. 11.

The number of pixels of the image sensor 16 shown in FIG. 12, i.e., the number of pixels 26 of the image sensor 16, is 20×20. The 20×20 nitrogen-vacancy pairs 25 of the diamond crystal respectively correspond to these pixels 26.

The block size of the image sensor 16, i.e., the number of pixels 26 of each block 41 of the image sensor 16, is 4×4. That is, FIG. 12 shows an example of two-dimensional measurement with a resolution of 5×5 pixels.

There are four types of orientations of the nitrogen-vacancy pairs 25 in one block 41. Therefore, assume that the time required for the convergence of integration of one pixel is represented by T, the time required for the image sensor 16 in FIG. 12 to perform magnetic field measurement with respect to all the pixels is given by 5×5×T×4=100T.

As described above, the magnetic measurement apparatus 10 in FIG. 11 can implement a spatial resolution on a block basis of the image sensor 16, and hence can further improve the efficiency of magnetic measurement.

(Third Embodiment)

<Example of Configuration of Magnetic Measurement Apparatus>

Figure 13:
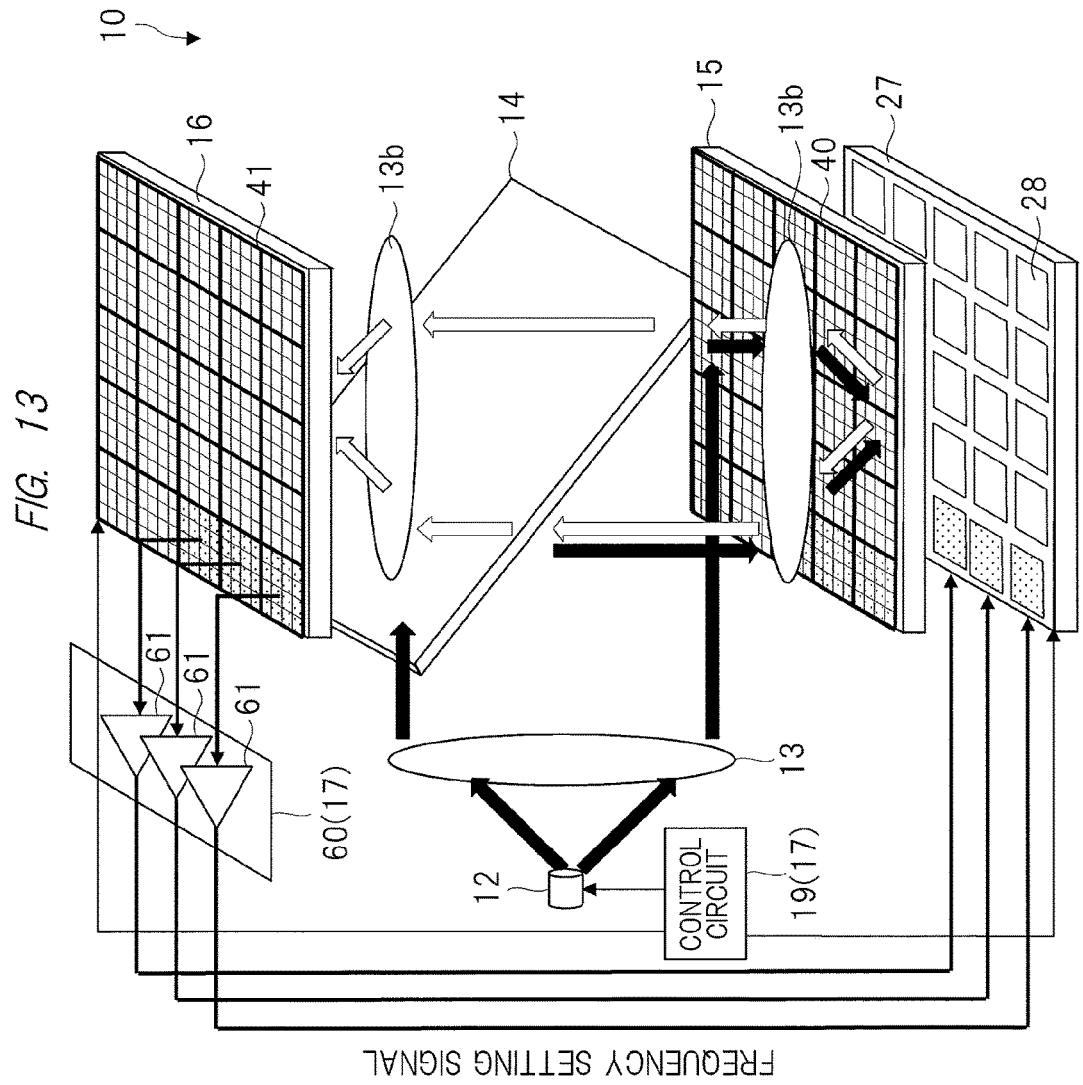
FIG. 13 is an explanatory view showing an example of the configuration of a magnetic measurement apparatus according to a third embodiment.

FIG. 13 is an explanatory view showing an example of the configuration of a magnetic measurement apparatus 10 according to a third embodiment.

The magnetic measurement apparatus 10 shown in FIG. 13 is provided with a high-frequency circuit chip 27 as an irradiation unit in place of the microwave source 20 in the configuration of FIG. 11 in the second embodiment. In addition, a control unit 17 is constituted by a signal processing array 60 and a control circuit 19.

The signal processing array 60 includes a plurality of signal processing units 61. Each signal processing unit 61 is constituted by a signal processing circuit 18 and an operation unit OPN which are shown in FIG. 11. Note that FIG. 13 shows the connection relationship between the three signal processing units 61 as a typical example. In practice, the signal processing units 61 are respectively provided for the blocks 41 of an image sensor 16.

<Example of Connection between Signal Processing Circuits>

Figure 14:
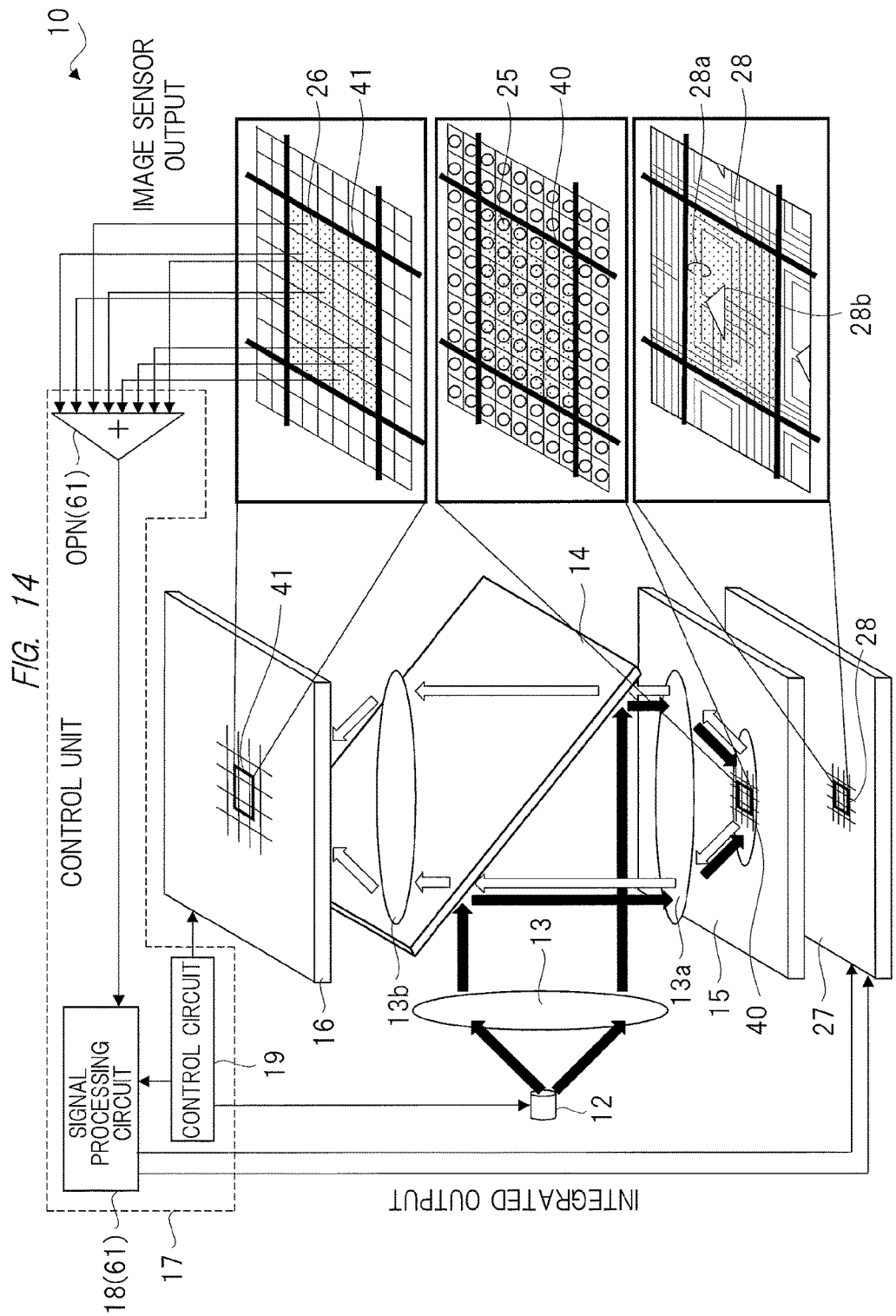
FIG. 14 is an explanatory view showing an example of the connection of a signal processing unit of the magnetic measurement apparatus in FIG. 13.

FIG. 14 is an explanatory view showing an example of the connection between the signal processing units 61 of the magnetic measurement apparatus 10 in FIG. 13. The left side of FIG. 14 shows the configuration of the magnetic measurement apparatus 10. A portion extending from the upper to the lower of the right side of FIG. 14 shows enlarged views of a block 41 of the image sensor 16, a block 40 of a diamond crystal 15 corresponding to the block 41, and a high-frequency circuit portion 28 (described later) corresponding to the block 40.

The signal processing unit 61 includes the signal processing circuit 18 and the operation unit OPN. The operation unit OPN symbolically represents the processing of adding pixel outputs from the image sensor 16 corresponding to nitrogen-vacancy pairs 25 having the same orientation for each block 41. Therefore, the operation unit OPN adds outputs, of outputs serially read out from the respective pixels of a given block 41 of the image sensor 16, which correspond to the nitrogen-vacancy pairs 25 having the same orientation.

The addition value obtained by the operation unit OPN is input to the signal processing circuit 18. The processing performed by the signal processing circuit 18 is the same as that in the second embodiment. The integrated output from the signal processing circuit 18 is input as a frequency setting signal to the high-frequency circuit chip 27.

The high-frequency circuit chip 27 irradiates the diamond crystal 15 with, for example, microwaves of about 2.87 GHz. The high-frequency circuit chip 27 is arranged near the lower portion of the diamond crystal 15.

The high-frequency circuit chip 27 is provided with a plurality of high-frequency circuit portions 28 in a lattice pattern. The high-frequency circuit portions 28 are provided by the same number of blocks 40 of the diamond crystal 15. In other words, the high-frequency circuit portions 28 are provided in correspondence with the respective blocks 40 of the diamond crystal 15. There is a 1:1:1 correspondence among the number of blocks 41 of the image sensor 16, the number of blocks 40 of the diamond crystal 15, and the number of signal processing units 61 of the signal processing array 60.

The high-frequency circuit portions 28 irradiate the blocks 40 of the diamond crystal 15 with microwaves from the lower surface side of the diamond crystal 15. The frequency of microwaves applied by each high-frequency circuit portion 28 is modulated by the frequency setting signal output from the respective signal processing units 61.

Each high-frequency circuit portion 28 includes a loop antenna 28a and a high-frequency circuit 28b which applies a high-frequency current to the loop antenna 28a.

Using the high-frequency circuit chip 27 makes it possible to parallelly irradiate the diamond crystal 15, for each set of a plurality of blocks 40, with independent microwaves. This can improve the efficiency of magnetic measurement.

In the case shown in FIG. 13, the number of pixels of the image sensor 16 is 20×20, and the number of nitrogen-vacancy pairs of the diamond crystal 15 is 20×20. In addition, the numbers of blocks of the image sensor 16 and diamond crystal 15 are both 5×5. Therefore, the number of signal processing units 61 is also 5×5.

<Example of Configuration of High-Frequency Circuit Chip>

Figure 15A:
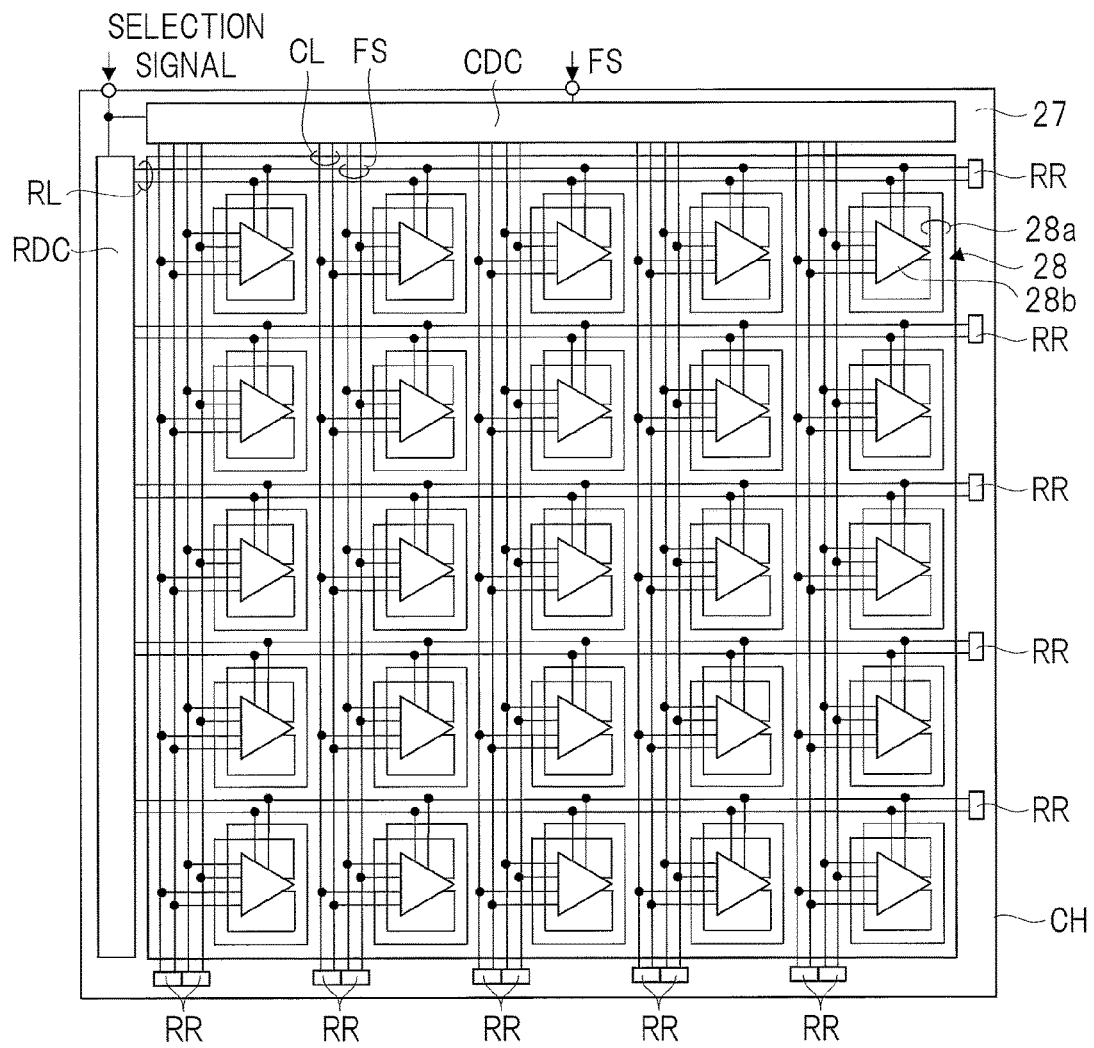
FIGS. 15A and 15B are explanatory views each showing an example of the configuration of a high-frequency circuit chip provided in the magnetic measurement apparatus in FIG. 13.
Figure 15B:
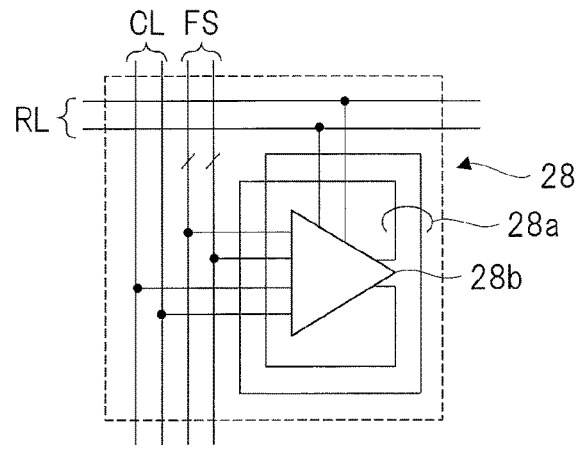

FIGS. 15A and 15B are explanatory views showing an example of the configuration of the high-frequency circuit chip 27 provided in the sensor unit 10 in FIG. 13. FIG. 15 exemplifies the high-frequency circuit chip 27 corresponding to the image sensor 16 shown in FIG. 13. The high-frequency circuit chip 27 has undergone, for example, a dual wiring process for noise reduction.

As shown in FIG. 15A, the high-frequency circuit chip 27 corresponds to the number of blocks of the image sensor 16. The number of high-frequency circuit portions 28 is 5×5. The high-frequency circuit chip 27 is obtained by forming and arranging the high-frequency circuit portions 28 on, for example, a semiconductor chip CH.

As shown in FIG. 15B, each high-frequency circuit portion 28 includes the loop antenna 28a and the high-frequency circuit 28b. As described above, the microwaves generated by the high-frequency circuits 28b are respectively and individually modulated by frequency setting signals output from the signal processing units 61 corresponding to the high-frequency circuit portions 28.

A row decoder RDC for selecting a row address line RL and a column decoder CDC for selecting a column address line CL are respectively arranged on two peripheral portions of the semiconductor chip CH. Termination resistors RR are respectively connected to the ends of the row address lines RL and the column address lines CL. This can prevent the reflection of signals at the wiring ends and reduce noise.

The selection signals output from the control circuit 19 in FIG. 14 are respectively input to the row decoder RDC and the column decoder CDC. The row decoder RDC selects an arbitrary row address line RL based on the selection signal. The column decoder CDC selects an arbitrary column address line CL based on the selection signal.

Each row address line RL selects the high-frequency circuit portions 28 in the row direction from the high-frequency circuit portions 28 arranged in an array. Each column address line CL selects the high-frequency circuit portions 28 in the column direction.

A frequency setting signal is input to the column decoder CDC. The column decoder CDC outputs a frequency setting signal to the high-frequency circuit portions 28 in the column direction via a frequency setting signal line FS. The row decoder RDC selects an arbitrary row address line RL based on a selection signal. The column decoder CDC selects an arbitrary column address line CL based on a selection signal and outputs a frequency setting signal.

The high-frequency circuit portion 28 located at the intersection between the selected row address line RL and the selected column address line CL is selected and activated. In addition, a frequency setting signal is input to the selected high-frequency circuit portion 28 via the frequency setting signal line FS.

<Example of Microwave Irradiation>

Figure 16:
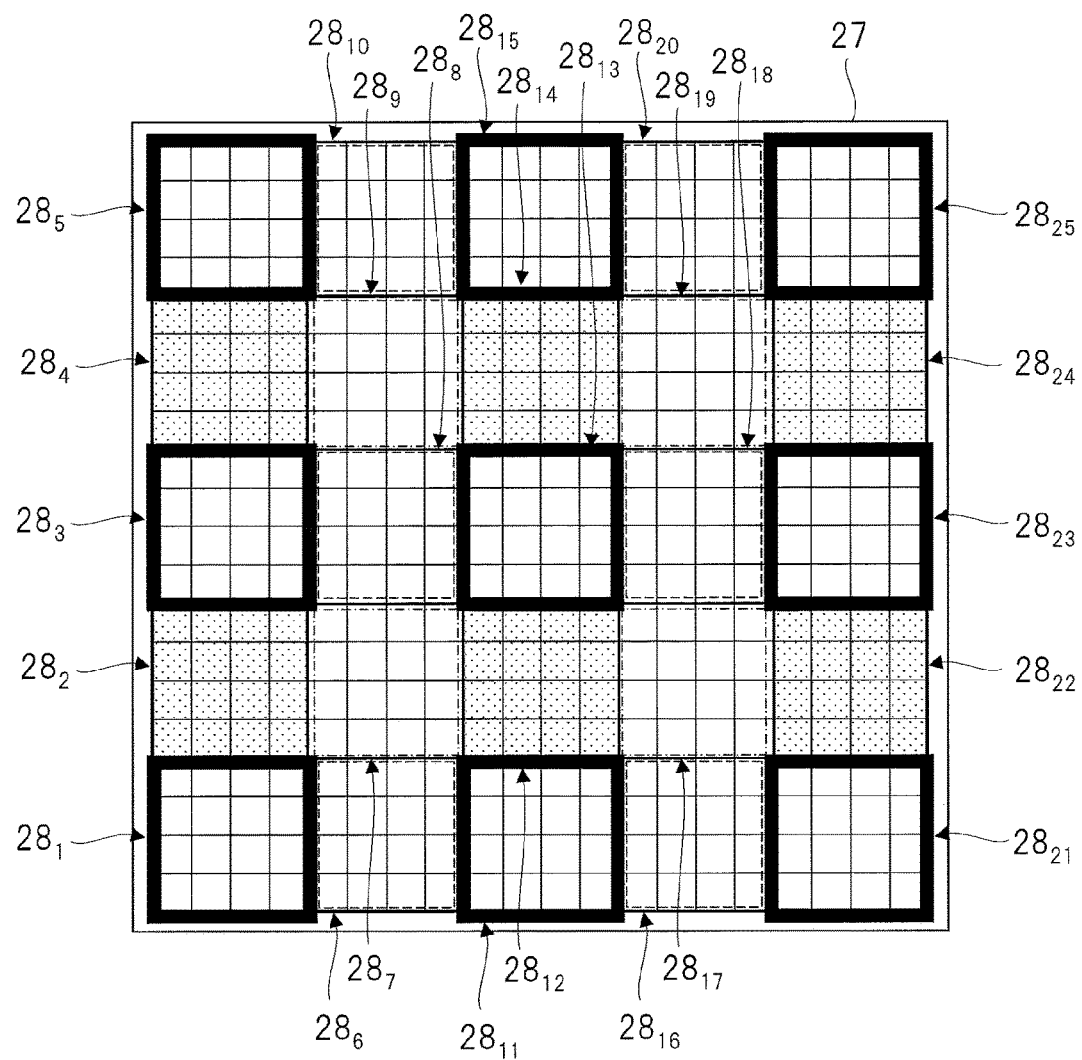
FIG. 16 is an explanatory view showing an example of the order of application of microwaves by the respective high-frequency circuit portions on the high-frequency circuit chip in FIG. 15.

FIG. 16 is an explanatory view showing an example of the order of microwave irradiation by the respective high-frequency circuit portions 28 of the high-frequency circuit chip 27 in FIG. 15.

Assume that, referring to FIG. 16, like FIG. 12, the diamond crystal 15 including the 20×20 nitrogen-vacancy pairs 25 corresponds to the image sensor 16 including 20×20 pixels. FIG. 16 shows a case in which two-dimensional measurement is performed with a block size of 4×4 and a resolution of 5×5. In addition, referring to FIG. 16, the high-frequency circuit portions 28 corresponding to the 25 blocks 40 in FIG. 16 will be referred to as high-frequency circuit portions $28_1$ to $28_{25}$.

Consider a case in which in the high-frequency circuit chip 27, the adjacent high-frequency circuit portions 28 simultaneously apply microwaves, for example, a case in which the high-frequency circuit portions $28_1$ and $28_2$ apply microwaves.

In this case, the boundary portion between the blocks in the diamond crystal 15 which correspond to the high-frequency circuit portions $28_2$ and $28_2$ simultaneously receives microwaves from the two high-frequency circuit portions. This may lead to a failure to implement high-accuracy measurement due to microwave interference or the like.

For this reason, when sharp measurement is to be performed, control is performed so as not to apply microwaves to adjacent blocks in one measurement. For example, the 25 high-frequency circuit portions, that is, the high-frequency circuit portions $28_2$ to $28_{25}$ are divided into four groups, i.e., the first to four groups, which are not adjacent to each other, and measurement is individually performed four times with respect to each group. Referring to FIG. 16, the first group is indicated by the thick lines, the second group is indicated by the hatchings, the third group is indicated by the dotted lines, and the fourth group is indicated by the chain lines. Measurement is simultaneously performed within each group. The high-frequency circuit portions 28 corresponding to the respective blocks 40 are respectively modulated by different microwaves.

As indicated by the thick lines in FIG. 16, the first group is constituted by the high-frequency circuit portions $28_1$, $28_3$, $28_5$, $28_{11}$, $28_{13}$, $28_{15}$, $28_{21}$, $28_{23}$, and $28_{25}$. As indicated by the hatchings in FIG. 16, the second group is constituted by the high-frequency circuit portions $28_2$, $28_4$, $28_{12}$, $28_{14}$, $28_{22}$, and $28_{24}$.

In addition, as indicated by the dotted lines in FIG. 16, the third group is constituted by the high-frequency circuit portions $28_6$, $28_8$, $28_{10}$, $28_{16}$, $28_{18}$, and $28_{20}$. As indicated by the chain lines in FIG. 16, the fourth group is constituted by the high-frequency circuit portions $28_7$, $28_9$, $28_{17}$, and $28_{19}$. Grouping the high-frequency circuit portions in this manner can prevent adjacent blocks from being irradiated with microwaves.

When irradiating the blocks belonging to each group described above with microwaves, assuming that the time required for the convergence of integration of one pixel is represented by T, the time required for magnetic field measurement with respect to all the pixels is given by 4×T×4 =16T.

Assume that measurement is performed by irradiating the 25 blocks 40 one by one with microwaves and performing negative feedback on image sensor outputs with respect to the microwave source without using the high-frequency circuit chip 27. In this case, the measurement time given by 5×5×T×4 =100T is required. Using the high-frequency circuit chip 27 can therefore speed up measurement by six times or more.

As has been described above, it is possible to speed up magnetic measurement.

As described above, the invention by the inventors has been specifically explained according to the embodiments, however, it is obvious that the invention is not limited to the embodiments and various changes may be made without departing from the scope of the invention.

The present invention is not limited to the foregoing embodiments and but includes various modification examples. For example, the above-described embodiment concretely described the present invention so that the present invention can be easily understood, and thus the present invention is not necessarily limited to the one including all the configurations described in the foregoing.

Part of the configuration of a certain embodiment can be replaced by the configuration of another embodiment, and the configuration of the other embodiment can be added to the configuration of the certain embodiment. Moreover, part of the configuration of the embodiment can be subjected to addition/deletion/replacement of other configurations.

What is claimed is:

1. A magnetic measurement apparatus comprising:
 a diamond crystal having a plurality of nitrogen-vacancy pairs;
 an image sensor configured to detect a fluorescence intensity generated by an exciting light applied to the diamond crystal by using a plurality of pixels;
 a microwave unit configured to irradiate the diamond crystal with microwaves based on an operation control signal, the microwave unit including a microwave source and a coil; and
 a control unit configured to integrate differences between fluorescence intensities output from the pixels corresponding to the nitrogen-vacancy pairs which have the same orientation among the nitrogen-vacancy pairs whose orientations have been specified, when microwaves are applied from the microwave unit and when no microwaves are applied therefrom, and output the calculation result as a frequency correction value,
 wherein the nitrogen-vacancy pairs of the diamond crystal are made to one-to-one correspond to the pixels, and fluorescence generated by one of the nitrogen-vacancy pairs is received by one of the pixels made to correspond to the nitrogen-vacancy pair,
 wherein a type of orientation of the vacancy of each of the nitrogen-vacancy pairs of the diamond crystal when viewed from the nitrogen thereof is specified with respect to an orientation of the diamond crystal, and
 wherein the microwave unit modulates a frequency of microwaves to be applied based on the frequency correction value output from the control unit, and
 wherein the control unit calculates the frequency correction value for each sensor block obtained by dividing the image sensor into a plurality of regions.

2. The apparatus according to claim 1,
 wherein the diamond crystal is a single crystal.

3. A magnetic measurement apparatus comprising:
 a diamond crystal having a plurality of nitrogen-vacancy pairs;
 an image sensor configured to detect a fluorescence intensity generated by an exciting light applied to the diamond crystal by using a plurality of pixels;
 an irradiation unit configured to apply microwaves from a lower surface of the diamond crystal; and
 a control unit configured to integrate differences between fluorescence intensities output from the pixels corresponding to the nitrogen-vacancy pairs which have the same orientation among the nitrogen-vacancy pairs whose orientations have been specified, when microwaves are applied and when no microwaves are applied, and output the calculation result as a frequency correction value,
 wherein the nitrogen-vacancy pairs of the diamond crystal are made to one-to-one correspond to the pixels, and fluorescence generated by one of the nitrogen-vacancy pairs is received by one of the pixels made to correspond to the nitrogen-vacancy pair,
 wherein a type of orientation of the vacancy of each of the nitrogen-vacancy pairs of the diamond crystal when viewed from the nitrogen thereof is specified with respect to an orientation of the diamond crystal,
 wherein the irradiation unit modulates a frequency of microwaves to be applied based on the frequency correction value output from the control unit,
 wherein the irradiation unit comprises a plurality of high-frequency circuit portions,
 the high-frequency circuit portions are provided in correspondence with blocks on the diamond crystal which are obtained by dividing the diamond crystal into a plurality of regions, and respectively modulate frequencies of microwaves to be applied based on the frequency correction values output from the control unit, and
 the control unit integrates differences for each block on the image sensor which is obtained by dividing the image sensor into a plurality of regions, and outputs the calculation results as frequency correction values to the high-frequency circuit portions which apply the microwaves to blocks on the diamond crystal which correspond to blocks of the image sensor having undergone the integration.

4. The apparatus according to claim 3,
wherein operations of the high-frequency circuit portions are controlled based on operation control signals output from the control unit, and
the control unit controls the operation control signals so as not to make the adjacent high-frequency circuit portions simultaneously apply the microwaves.

5. The magnetic measurement apparatus according to claim 1,
wherein the control unit includes any one of a group consisting of a signal processing circuit and a control circuit and a group consisting of a signal processing array and a control circuit.

6. The magnetic measurement apparatus according to claim 3,
wherein the control unit includes any one of a group consisting of a signal processing circuit and a control circuit and a group consisting of a signal processing array and a control circuit.

7. The apparatus according to claim 3,
wherein the diamond crystal is a single crystal.

* * * * *